(12) United States Patent
Reisner et al.

(10) Patent No.: US 11,609,236 B2
(45) Date of Patent: Mar. 21, 2023

(54) BLOOD BIOMARKERS FOR SEVERE TRAUMATIC BRAIN INJURIES

(71) Applicant: Children's Healthcare of Atlanta, Inc., Atlanta, GA (US)

(72) Inventors: Andrew Reisner, Atlanta, GA (US); Laura Blackwell, Atlanta, GA (US); Iqbal Sayeed, Atlanta, GA (US)

(73) Assignee: Children's Healthcare of Atlanta, Inc., Atlanta, GA (US)

( * ) Notice: Subject to any disclaimer, the term of this patent is extended or adjusted under 35 U.S.C. 154(b) by 428 days.

(21) Appl. No.: 16/593,372

(22) Filed: Oct. 4, 2019

(65) Prior Publication Data

US 2020/0110098 A1 Apr. 9, 2020

Related U.S. Application Data

(60) Provisional application No. 62/742,011, filed on Oct. 5, 2018.

(51) Int. Cl.
*G01N 33/68* (2006.01)

(52) U.S. Cl.
CPC ..... *G01N 33/6887* (2013.01); *G01N 2800/28* (2013.01); *G01N 2800/38* (2013.01)

(58) Field of Classification Search
CPC ........... G01N 33/6887; G01N 2800/28; G01N 2800/38; G01N 2800/52; G01N 33/6896
See application file for complete search history.

(56) References Cited

U.S. PATENT DOCUMENTS

| 2016/0103140 A1 | 4/2016 | Chodobski et al. |
| 2018/0059123 A1 | 3/2018 | Wang et al. |
| 2018/0106800 A1 | 4/2018 | Datwyler et al. |

FOREIGN PATENT DOCUMENTS

| WO | 2003019181 A2 | 3/2003 |
| WO | 2010006318 A2 | 1/2010 |

OTHER PUBLICATIONS

Ahmed et al., ("The temporal pattern of changes in serum biomarker levels reveals complex and dynamically changing pathologies after exposure to a single low-intensity blast in mice," Publ. Jun. 12, 2015, Frontiers in Neurology, vol. 6, DOI: 10.3389/fneur.2015.00114. (Year: 2015).*
International Search Report and Written Opinion issued in International Application No. PCT/US19/54724, dated Jan. 2, 2020 (12 pages).
(Continued)

*Primary Examiner* — Jennifer Wecker
*Assistant Examiner* — Michael Paul Shimek
(74) *Attorney, Agent, or Firm* — Morris, Manning & Martin, LLP; Daniel E. Sineway, Esq.

(57) ABSTRACT

Disclosed herein is the use of plasma osteopontin (OPN) levels for diagnosing and predicting the severity and outcomes in traumatic brain injury (TBI), such as adult and pediatric TBI. The disclosed method can be used to diagnose TBI in any subject, such as pediatric, adult, and geriatric subjects. However, the method is particularly useful in pediatric subjects where current methods are insufficient. A particularly useful advantage of the disclosed methods is the ability to diagnose Abusive Head Trauma (AHT) in a pediatric subject.

22 Claims, 15 Drawing Sheets

(56) References Cited

OTHER PUBLICATIONS

Ahmed, F., et al., The Temporal Pattern of Changes in Serum Biomarker Levels Reveals Complex and Dynamically Changing Patholigies after Exposure to a Single Low-Intensity Blast in Mice, Frontiers in Neurology, Jun. 12, 2015; vol. 6, No. 114; pp. 1-14.

Araki, T., et al., Pediatric Traumatic Brain Injury: Characteristic Features, Diagnosis, and Management. Neurologia Medico-Chirurgica. Jan. 20, 2017; vol. 57, No. 2; pp. 82-93.

Yan, X., et al., Plasma Concentrations of Osteopontin, but not Thrombin-Cleaved Osteopontin, are Associated with the Presence and Severity of Nephropathy and Coronary Artery Disease in Patient with Type 2 Diabetes Mellitus. Cardiovascular Diabetology. Oct. 29, 2010; vol. 9, No. 70; pp. 1-8.

Wang, P. et al., Clinical Value of Combined Determination of Serum B7-H4 with Carcinoembryonic Antigen, Osteopontin, or Tissue Polypeptide-Specific Antigen for the Diagnosis of Colorectal Cancer, Disease Markers. Sep. 2018, No. 4310790; pp. 1-9.

Antonios, A., et al., Osteopontin as Indicator of Traumatic Brain Injury Severity and Progression. 3rd International Conference on Neurological Disorders and Brain Injury. Apr. 2017; retrieved from the internet https://www.longdom.org/proceedings/osteopontin-as-indicator-of-traumatic-brain-injury-severity-and-progression-18117.html on Jan. 2, 2020; p. 1.

Chia-Yi, Kuan, et al., "Osteopontin as a Blood Biomarker in Traumatic Brain Injury and Hypoxic-Ischemic Encephalopathy," 34th Annual National Neurotrauma Symposium, Lexington, KY (Jun. 26-29, 2016), retrieved from the internet at https://www.liebertpub.com/doi/full/10.1089/neu.2016.29008.abstracts on Jun. 27, 2022, pp. 30-31.

Extended European Search Report issued in European Application No. 19868320, dated Jun. 15, 2022.

Chan, et al., "Osteopontin expression in acute immune response mediates hippocampal synaptogenesis and adaptive outcome following cortical brain surgery", Experimental Neurology, Nov. 2010, vol. 261, Nov. 1, 2024, pp. 757-771.

\* cited by examiner

BLOOD BIOMARKERS FOR SEVERE TRAUMATIC BRAIN INJURIES

CROSS-REFERENCE TO RELATED APPLICATIONS

This application claims benefit of and priority to U.S. Provisional Application No. 62/742,011, filed Oct. 5, 2018, which is hereby incorporated herein by reference in its entirety.

STATEMENT REGARDING FEDERALLY SPONSORED RESEARCH OR DEVELOPMENT

This invention was made with Government Support under Grant No. NS103597 awarded by the National Institutes of Health. The Government has certain rights in the invention.

BACKGROUND

Traumatic brain injury (TBI) is the leading cause of death and disability among young adults in the United States and worldwide (Prevention CfDCa. Surveillance Report of Traumatic Brain Injury-related Emergency Department Visits, Hospitalizations, and Deaths—United States, 2014. Centers for Disease Control and Prevention, U.S. Department of Health and Human Services 2019). Rapid stratification of TBI severity in patients is of great importance to provide prognostic information and to make treatment decisions soon after TBI (Hergenroeder G W, et al. Mol Diagn Ther. 2008 12(6):345-58). However, existing methods to predict TBI outcome have not had a widespread impact on clinical practice because they depend upon clinical and imaging findings that are not always consistently available in the acute setting. Further, even when available, the clinical course, treatment needed and prognosis varies among patients even if their presenting features and radiographic studies are similar. Identifying accurate, noninvasive and cost-effective diagnostic methodologies for patients with brain injury is recognized as an urgent need by clinicians and scientists alike. Patients who have suffered a moderate-to-severe TBI still lack an effective and reliable treatment that will enhance the processes underlying functional recovery. Factors contributing to this situation include failure to use prognostic indicators and surrogate biomarkers to better define the target population for testing a potential intervention and reliably identifying a treatment effect.

TBI is also the leading cause of death and disability in children. In 2013, there were nearly 2.8 million TBI-related emergency department visits, hospitalization, and deaths (TBI-EDHDs) in the United States. Among them, 23.6% fell into the 0-14 years of age group (Taylor C A, et al. MMWR Surveil) Summ 2017 66(9):1-16). Because mature and developing brains have different physiological and metabolic properties, specific guidelines are recommended for the monitoring and clinical management of pediatric TBI (Giza C, et al. Curr Opin Crit Care 2007 13:143-52; Au A K, et al. Curr Opin Neurol 2017 30:565-572). For example, though several adult TBI studies have indicated a correlation between elevated plasma GFAP levels and CT-evidenced intracranial lesions at emergency department, this association was not found in children with TBI (Okonkwo D O, et al. J Neurotrauma 2013 30:1490-1497; Mondello S, et al. Science Report 2016 6:28203). In fact, there are no established blood biomarkers to assist the diagnosis and prognosis in pediatric TBI.

The current approach to identify blood biomarkers in TBI emphasizes measuring neuron or astrocyte-specific proteins released to the blood after brain damage (Adrian H, et al. eNeuro 2016 e0294-16 2016 1-13). Despite a sound rationale, the brain-to-blood release of neuron/astrocyte-specific markers depends in-part on glymphatic transport that could be attenuated by TBI-induced intracranial pressure or clinical management (Plog B A, et al. J Neurosci 2015 35:518-526). In addition, the stability of neuron/astrocyte-specific proteins in the blood is generally unknown. These factors may explain why the plasma GFAP level peaks within 24 hours of TBI onset, making it less suitable to monitor the evolution of brain damage (Adrian H, et al. eNeuro 2016 e0294-16 2016 1-13).

Therefore, there is a long-felt but unresolved need for a blood biomarker that can readily and effectively identify the severity of a traumatic brain injury, and thus provide meaningful guidance with respect to treatment of the same.

SUMMARY

Disclosed herein is the use of plasma osteopontin (OPN) levels for predicting the severity and outcomes in TBI, such as adult and pediatric TBI. OPN, also called Secreted Phosphoprotein 1 (SSP1), belongs to the small integrin-binding ligand N-link glycoprotein (SIBLINGs) family and exhibits high stability in the blood and saliva (Bellahcene A, et al. Nature Reviews Cancer 2008 8:212-226; Lanteri P, et al. Clin Chem Lab Med 2012 50:1979-1984; Gopal N, et al. J Clin Diagn Res 2016 10:BC06-08). The baseline level of OPN is negligible in healthy brains, but it is upregulated in activated microglia and macrophages in a broad spectrum of brain pathologies, including neonatal hypoxia-ischemia, stroke, electrolytic lesion, TBI, and Alzheimer's models (Ellison J A, et al. Stroke 1998 29:1698-1706; Chen W, et al. Stroke 2011 42:764-769; van Velthoven C T, et al. Stroke 2011 42:2294-2301; Li Y, et al. eNeuro 2017 4(1). pii: ENEURO.0253-16.2016; Chan J L, et al. Exp Neurol 2014 261:757-771; von Gertten C, et al. BMC Neurosci 2005 6:69; Rentsendorj A, et al. Brain Behav Immun 2017 67:163-180). As disclosed herein, OPN is a useful blood biomarker for the diagnosis and prognosis of TBI (FIG. 1A).

Therefore, disclosed herein is a method for providing a diagnosis or prognosis of a subject with a head injury that involves providing a biological sample from the subject, such as blood, plasma, serum, urine, sputum, or perspiration, determining the concentration of osteopontin (OPN) in the sample, and comparing the determined OPN concentration with at least one reference value. In some embodiments, an elevated OPN value is an indication that the subject has a traumatic brain injury (TBI).

The disclosed method can be used to diagnose TBI in any subject, such as pediatric, adult, and geriatric subjects. However, the method is particularly useful in pediatric subjects where current methods are insufficient. A particularly useful advantage of the disclosed methods is the ability to differentiate between Abusive Head Trauma (AHT) and accidental injury in a pediatric subject.

In some embodiments, the subject has a head injury, with or without a fracture or penetration of the skull. In all cases of trauma, the method can be used to determine whether the injury has resulted in neuroinflammation consistent with TBI. In other embodiments, the subject does not have visible signs of head injury, but is a candidate for a closed head injury. For example, the subject could have been in an accident causing rapid acceleration or deceleration of the head but is not yet experiencing symptoms of TBI. Alternatively, the subject can be experiencing neurological symptoms without indication of the cause, such as in the case of a potential abuse victim. For example, the subject could be experiencing symptoms of TBI, such as confusion, disorientation, difficulty remembering new information, headache, dizziness, blurry vision, nausea, or vomiting. The disclosed method can be used to diagnose TBI, determine the severity of TBI, and/or predict whether it is due to a single trauma or repeated trauma.

The disclosed methods involve comparing OPN values in a bodily fluid to reference values to identify subjects with elevated OPN. Reference values can be empirically determined from age-matched controls. For example, in some embodiments, the reference value is the median OPN concentration of control samples of a group of control subjects. In some embodiments, the reference value is an OPN cut-off value determined by a receiver operating curve (ROC) analysis from biological samples of one or more subject groups. In some embodiments, the OPN cut-off value is at least twice the value of the control sample. In some embodiments, OPN value is also predictive of the severity of TBI. Therefore, in some embodiments multiple OPN-cutoff values are determined and used to stratify subjects. In some embodiments, the OPN cut-off value is at least 100 ng/ml in blood, serum, or plasma.

The disclosed method can also involve the use of other TBI biomarkers to increase the accuracy of diagnosis and stratification of TBI severity and outcome characterization. For example, in some embodiments, the method further involves determining in the sample the concentration of GFAP, UCH-L1, S-110, inflammatory cytokines, or a combination thereof.

Also disclosed is a method for treating TBI in a subject that involves providing a biological sample from the subject, such as blood, plasma, serum, urine, sputum, or perspiration, determining the concentration of osteopontin (OPN) in the sample, comparing the determined OPN concentration with at least one reference value, detecting an elevated OPN value in the sample, and treating the subject for TBI.

Also disclosed herein is a kit for diagnosing brain injury, comprising antibodies for specifically quantifying OPN concentration in a biological sample of a subject, loading control antibodies, and standards for creating a standard curve. The kit can also contain antibodies for quantifying one or more other biomarkers of TBI. The kit can also contain reference values for determining if the OPN values are elevated and by how much. These reference values can be contained in a electronic medium for use by software configured to compare OPN levels and provide a risk score.

The details of one or more embodiments of the disclosure are set forth in the accompanying drawings and the description below. Other features, objects, and advantages of the disclosure will be apparent from the description and drawings, and from the claims.

DESCRIPTION OF DRAWINGS

FIG. 1A is a schematic diagram of using plasma OPN levels to predict the severity and outcomes of TBI. FIG. 1B shows immunoblot analysis demonstrated clear induction of OPN, MMP-9 and GFAP in the ipsilateral hemisphere of one-month-old mice with a low 2) or high (3-4) neurologic severity score (NSS) at 48 h after CCI. Shown are the results of two representative mice for n>6 in each group. Shams were age-matched mice subjected to craniotomy without CCI. rOPN: mouse recombinant OPN used as positive controls. FIG. 1C is immunostaining showing induction of OPN in GFP- and F4/80-positive, activated microglia or macrophages (arrows) in the ipsilateral, but not the contralateral hemisphere of CX3CR1GFP/+ mice at 48 h post-CCI. FIG. 1D shows few anti-OPN immunosignals were detected in GFAP-positive astrocytes in ipsilateral or contralateral hemisphere at 48 h after CCI. Shown are the representative images in n>3 animals. Scale bar: 20 μm.

FIG. 2A is immunoblotting showing induction of plasma OPN and GFAP, but not MMP-9, in CCI-injured one-month-old mice exhibiting high-, but not low-NSS, at 48 h recovery. Shown are the results of three representative low-NSS and high-NSS mice (n>6 examined for each group). rOPN: mouse recombinant OPN used as positive controls. FIG. 2B shows quantification of immunoblot signals revealing a significantly higher level of plasma OPN and GFAP in high-NSS than in low-NSS mice. FIG. 2C shows ELISA (Luminex) corroborated significant induction of plasma OPN levels in high-NSS mice compared with low-NSS mice at 48 h post after CCI (n=3). The p-value was determined using t-test.

FIG. 3A is a scatter plot of the plasma OPN and GFAP levels upon admission in pediatric TBI patients with and without intracranial lesions on CT. The p-value was determined by Mann-Whitney test between 19 CT-negative and 46 CT-positive cases. FIG. 3B is a scatter plot of the plasma OPN and GFAP levels at admission in children suffered from mild (GCS 13-15, n=11), moderate (GCS 9-12, n=5) or severe TBI (GCS 3-8, n=50). The p-value was determined by Mann-Whitney test. The Receiver Operating Characteristic (ROC) graph of using plasma OPN or GFAP levels at admission to diagnose severe TBI. The area under curve in ROC graph is 0.73 for OPN (p=0.02), and 0.53 for GFAP (p=0.7435).

FIG. 4A is a comparison of the highest plasma OPN or GFAP levels within 72 hours of hospitalization between children with severe TBI that later survived (n=19) or deceased (n=5). The p-value was determined by Mann-Whitney test.

FIG. 4B shows correlation analysis of the highest plasma OPN or GFAP levels within 72 hours of hospitalization with the eventual days that required ventilator support during hospitalization in children with severe TBI (n=16). The Spearman's rank correlation coefficient (r) is 0.7049 for OPN (p=0.0008), and −0.1765 for GFAP (p=0.4699). FIG. 4C shows in the same cohort of severe TBI patients, correlation coefficient (r) between the highest plasma OPN levels within 72 hours of TBI-onset and the in-ICU days in hospitalization is 0.6112 for OPN (p=0.0054), and 0.0440 for GFAP (p=0.8579). The p-value was determined by Mann-Whitney test.

FIG. 6A is a scatter plot of 30 patients showing sustained increase in OPN level at 24 and 48 compared to baseline at the time of admission. FIG. 6B shows mean serum OPN levels markedly increase in moderate-severe and severe groups compared to moderate group.

DETAILED DESCRIPTION

Figure 1A:
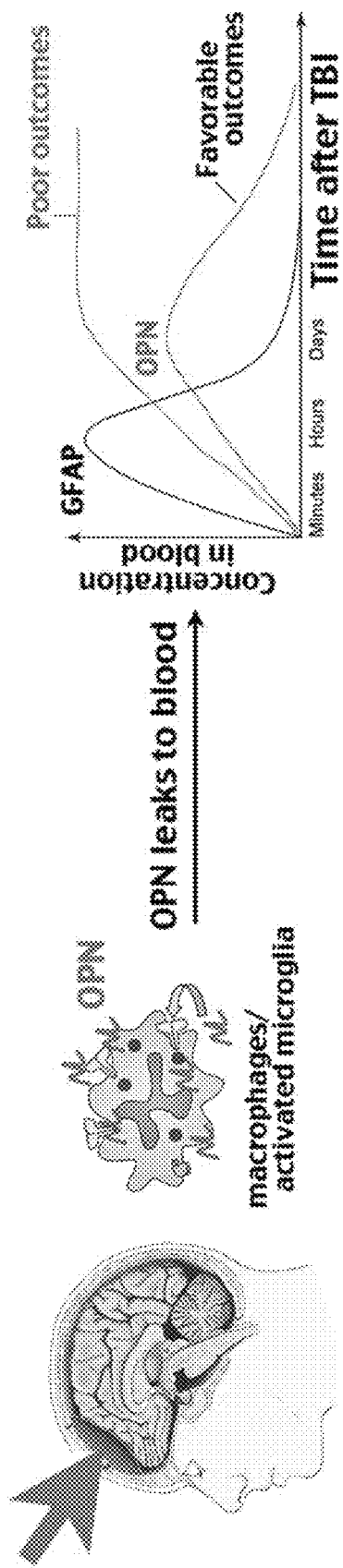
FIGS. 1A to 1D show induction of brain injury markers after controlled cortical impact (CCI) in juvenile mice.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

Definitions

The term "antibody" refers to natural or synthetic antibodies that selectively bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that selectively bind the target antigen.

The term "brain injury" as used herein refers to any and all injury of the brain, which can be caused by fracture or penetration of the skull or a closed head injury such as in the case of rapid acceleration or deceleration of the head.

The term "sample from a subject" refers to a body fluid sample from a subject. Non-limiting examples of body fluids include blood, plasma, serum, urine, sputum, and perspiration.

The term "specifically binds", as used herein, e.g. when referring to an antibody, refers to a binding reaction which is determinative of the presence of the protein in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to OPN) when it does not bind in a significant amount to other proteins present in the sample or to other proteins to which the ligand or antibody may come in contact in an organism. Generally, a first molecule that "specifically binds" a molecule has a dissociation constant (Kd) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower Kd.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician. As used herein, the term "pediatric subject" as used herein refers to a subject age 0 to 18 years.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

Patients

The disclosed compositions, systems, kits, and methods can be used to diagnose and treat subjects with a traumatic brain injury (TBI). TBI can result from a closed head injury or a penetrating head injury. A closed injury occurs when the head suddenly and violently hits an object but the object does not break through the skull. A penetrating injury occurs when an object pierces the skull and enters brain tissue. Skull fractures occur when the bone of the skull cracks or breaks. A depressed skull fracture occurs when pieces of the broken skull press into the tissue of the brain. A penetrating skull fracture occurs when something pierces the skull, such as a bullet, leaving a distinct and localized injury to brain tissue. Skull fractures can cause cerebral contusion.

TBI results in neurodegeneration which is the progressive loss of neurons in the brain. Multiple physiological events lead to the neurodegeneration of the brain tissues following a traumatic injury. These events include, for example, cerebral edema, destruction of vascular integrity, increases in the immune and inflammatory response, demyelinization, and lipid peroxidation. However, it is often very difficult to assess a patient for brain injury in the first 24-72 hours. The disclosed methods can be used to diagnose injury early, and are therefore useful in reducing and/or preventing the physiological events leading to such neurodegeneration. Specifically, the present disclosure provides methods for reducing or eliminating neuronal cell death (directly or indirectly), edema, ischemia, and enhancing tissue viability following a traumatic injury to the central nervous system.

In some embodiments, the subject is a pediatric subject. TBI is the leading cause of death and disability in children. Pediatric TBI is associated with several distinctive characteristics that differ from adults and are attributable to age-related anatomical and physiological differences, pattern of injuries based on the physical ability of the child, and difficulty in neurological evaluation in children. Evidence suggests that children exhibit a specific pathological response to TBI with distinct accompanying neurological symptoms, and considerable efforts have been made to elucidate their pathophysiology.

Therefore, in some embodiments, the pediatric subject of the disclosed methods is 0-18, including 0, 1, 2, 3, 4, 5, 6, 7, 8, 9, 10, 11, 12, 13, 14, 15, 16, 17, or 18 years of age. In some embodiments the pediatric subject is 0-2, 0-4, 0-6, 0-8, 0-10, 0-12, 0-14, 0-16, 0-18, 2-4, 2-6, 2-8, 2-10, 2-12, 2-14, 2-16, 2-18, 4-6, 4-8, 4-10, 4-12, 4-14, 4-16, 4-18, 6-8, 6-10, 6-12, 6-14, 6-16, 6-18, 8-10, 8-12, 8-14, 8-16, 8-18, 10-12, 10-14, 10-16, 10-18, 12-14, 12-16, 12-18, 14-16, 14-18, or 16-18 years of age.

Abusive head trauma (AHT) is an injury to a child's brain as a result of child abuse. It can be caused by direct blows to the head, dropping or throwing a child, or shaking a child. AHT is also called shaken baby syndrome (or SBS), inflicted traumatic brain injury, and shaken impact syndrome. Head trauma is the leading cause of death in child abuse cases in the United States. Because the anatomy of infants puts them at particular risk for injury from this kind of action, the majority of victims are infants younger than 1 year old. AHT can happen in children up to 5 years old, but the average age of victims is between 3 and 8 months. The highest rate of cases is among infants just 6 to 8 weeks old, which is when babies tend to cry the most. In some embodiments, the disclosed methods can be used to distinguish between a subject, such as a pediatric subject, that has suffered a single head trauma from a subject that has suffered repeated head traumas.

In some embodiments, the subject is an adult subject. For example, the subject can be at least 18, 19, 20, or 21 years of age. In some embodiments, the subject is 18-20, 18-30, 18-40, 8-50, 18-60, 18-70, 18-80, 31-40, 31-50, 31-60, 31-70, 31-80, 41-50, 41-60, 41-70, 41-80, 51-60, 51-70, 51-80, 61-70, 61-80, 71-80, or at least 81 years of age.

Osteopontin Detection

Osteopontin (OPN) can be detected from a biological sample using techniques known in the art. In some embodiments, the biological sample is blood, plasma, serum, urine, sputum, or perspiration, thus obviating the need for painful and dangerous collection methodologies, such as spinal taps for spinal fluid.

Osteopontin (OPN) according to the present disclosure refers to a 32 kDa glycoprotein with mammalian origin, preferably human OPN. OPN is expressed in various cell types, including cardiomyocytes, osteoblasts, vascular muscle cells and fibroblasts. OPN can be present in the extracellular matrix as well as in a soluble form. OPN contains an RGD (arginine-glycin-aspartate) binding sequence that mediates interaction with several surface receptors, e.g. integrins, including β1-integrin. Osteopontin is a single-chain polypeptide composed of about 300 amino acids residues and has about 30 carbohydrate residues attached, including 10 sialic acid residues. The protein is rich in acidic residues: 30-36% are either aspartic or glutamic acid. In some embodiments, the amino acid sequence of human OPN is described in Genbank accession number NM_001040060.

Furthermore, two splice variants of human OPN have been described which differ from one another by the presence or absence of 14 amino acids after position 58 in the pre-signal-processed protein. CC1074 is the fully active mature chain (aa 17-314) which contains the full sized splice variant at aa 59-72 (see Protein accession number S09575). In some embodiments, the disclosed methods involve determining the concentration of human OPN in the soluble form.

In some embodiments, the determined OPN concentration, i.e. the measured Osteopontin concentration, is compared with at least one reference value. "Reference value" is a term used in medicine to denote a laboratory value used as a reference for values/data obtained by laboratory examinations of patients or samples collected from patients. In some embodiments, the reference value is the OPN concentration of a control sample or an OPN cut-off value.

A control sample can be selected from the biological sample of a control subject, or biological samples of a group of control subjects. A "control subject" can be a subject, e.g. a patient, of similar age without any brain injury. The OPN concentration of a control sample can be the median OPN concentration of control samples of a group of control subjects, i.e. the mean value of the OPN concentrations of control samples of a group of control subjects. A median OPN concentration can be obtained from a group of at least 20 control subjects, more preferably at least 30, even more preferably at least 40. The median OPN concentration can be the median OPN plasma concentration of a control sample.

In some embodiments, the OPN level of the control adult sample is about 0 ng/ml to 65 ng/ml. In some embodiments, the median OPN plasma level of the control adult sample is about 23.56±19.73 ng/mL (Al-Zoubi S, et al. Gastroenterol Hepatol Bed Bench. 2017 10(2):97-101).

In some embodiments, the OPN level of the control pediatric sample is about 0 ng/ml to 25 ng/ml. In some embodiments, the median OPN plasma level of the control pediatric sample is about 7.5 ng/ml (Rullo O J, et al. Arthritis Res Ther. 2013 15(1):R18).

In some embodiments, the OPN level of a subject with a brain injury is at least 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, 20 times that of an age-matched control value. Therefore, in some embodiments, the OPN value for an adult subject with a brain injury is at least 100 ng/ml, 150 ng/ml, 200 ng/ml, 250 ng/ml, 300 ng/ml. In some embodiments, the OPN value for a pediatric subject with a brain injury is at least 50 ng/ml, 75 ng/ml, 100 ng/ml, 125 ng/ml, 150 ng/ml. 175 ng/ml, 200 ng/ml, 250 ng/ml, 300 ng/ml, 350 ng/ml, 400 ng/ml.

In some embodiments, the OPN value is used to predict the severity of TBI. For example, in some embodiments moderate and severe TBI can be distinguished from mild TBI based on OPN values. FIG. 3 shows examples of OPN levels at admission for subjects less than 18 years of age with mild, moderate and severe TBI. Therefore, in some embodiments, for subjects of this age group, an OPN value of at least 300, 350, 400, 450, 500, 550, or 600 ng/ml at admission is an indication that the subject has moderate or severe TBI. In some embodiments, moderate and severe TBI can also be distinguished by OPN values either alone or in combination with one or more other biomarkers.

Figure 5:
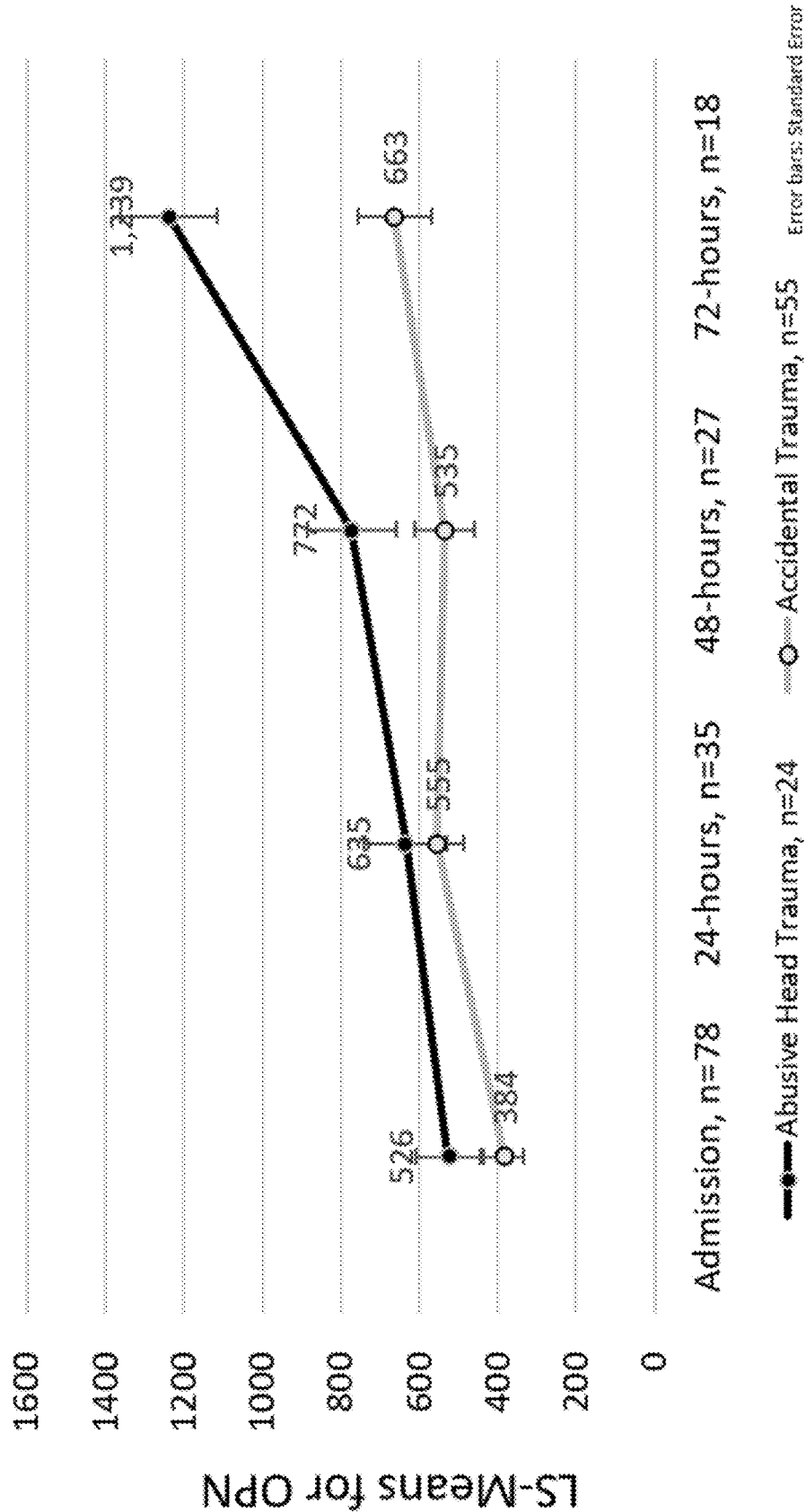
FIG. 5 shows mean values of OPN over time in abusive head injury versus accidental trauma. Error bars are representative of standard error values.

In some embodiments, the OPN value is used to differentiate between abusive head injury and accidental injury. For example, in some embodiments, the OPN value for a pediatric subject with AHT is at least 1.5, 2.0, 2.5, 3.0, 3.5, 4.0 times that of an age-matched subject with accidental (single) head trauma. FIG. 5 shows an example of OPN values over time in AHT versus accidental trauma in subjects less than 4 years of age. Therefore, in some embodiments, for subjects of this age group, an OPN value of at least 700, 800, 900, 1000, 1100, or 1200 ng/ml at about 72 hours post-admission is an indication that the subject has AHT. In some embodiments, the OPN value for a pediatric subject with AHT increases over time at a rate higher than in the case of an accidental head trauma. For example, as shown in FIG. 5, the rate of increase from 48 hours to 72 hours can be used to distinguish between accidental and abusive head trauma. Therefore, in some embodiments, an increase in OPN values from 48 to 72 hours of at least 30%, 35%, 40%, 45%, 50%, 55%, or 60% is an indication of AHT. It is understood that other time points after 24 hours and up to 3, 4, 5, 6, 7, 8, 9, or 10 days can be used to evaluate this change of over time.

In some embodiments, the OPN level from a brain injury depends on the amount of time that has lapsed since the head injury. Therefore, in some embodiments, the combination of OPN levels and time since head injury are used in combination to predict brain injury.

In some embodiments the reference value is an OPN cut-off value. In some embodiments, the OPN cut-off value is determined by a statistical classification method, such as receiver operating curve (ROC) analysis, from biological samples of a patient group. The biological samples are preferably plasma samples. Receiver Operating Curve (ROC) analysis is known in the art of medicine. Briefly, the ability of a test to discriminate diseased cases from normal cases is evaluated using Receiver Operating Characteristic (ROC) curve analysis. ROC curves can also be used to compare the diagnostic performance of two or more laboratory or diagnostic tests. When the results of a particular test in two populations is considered, one population with a disease, the other population without the disease, a perfect separation between the two groups is rarely observed. Indeed, the distribution of the test results will overlap.

Reagents for detecting OPN, such as ELISA kits, are commercially available. For example, ELISA kits for detecting human OPN are provided by R&D Systems (Minneapolis, Minn.). The steps of various useful immunodetection methods have been described in the scientific literature, such as, e.g., Maggio et al., Enzyme-Immunoassay, (1987) and Nakamura, et al., Enzyme Immunoassays: Heterogeneous and Homogeneous Systems, Handbook of Experimental Immunology, Vol. 1: Immunochemistry, 27.1-27.20 (1986), each of which is incorporated herein by reference in its entirety and specifically for its teaching regarding immunodetection methods. Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

Other Diagnostic Factors

Area under the ROC Curve (AUC) of OPN alone and OPN combined with other panel of marker using receiver-operator characteristic (ROC) can in some embodiments be used to increase the predictive utility and accuracy of OPN in diagnosis and stratification of TBI.

In some embodiments, a multi-marker approach can be used to characterize TBI outcome, since a "biological signature" may prove more effective in encompassing the multisystemic character of secondary injury pathology, and may increase diagnostic and prognostic accuracy. For example, admission blood levels of s100B and glial fibrillary acidic protein (GFAP) together accurately discerned survivors from non-survivors 1 year following TBI (Gradisek P, et al. Brain Inj 2012 26:1472-81). Combination of ubiquitin C-terminal hydrolase-1 (UCH-L1) and GFAP out performed either marker individually in discriminating TBI patients from healthy controls (Diaz-Arrastia R, et al. J Neurotrauma 2014 31:19-25).

However, these studies did not include markers reflecting additional secondary injury processes such as inflammation and oxidative damage. In view of this, a multivariate approach to TBI diagnosis has been reported that simultaneously assesses seven blood biomarkers, each associated with a specific TBI-related injury process: NSE relating to neuronal injury; brain-derived neurotrophic factor (BDNF) for neuronal repair; peroxiredoxin (PRDX)-6 for oxidative damage; GFAP and s100B for glial damage; monocyte chemoattractant protein (MCP)-1 for immune activation; intercellular adhesion molecule (ICAM)-5 for disruption of intercellular adhesion processes (Buonora J E, et al. Front Neurol 2015 6:68). However, while this multi-marker panel shows promise in acute TBI diagnosis, the prognostic utility of these markers for longer-term outcome in more severely injured patients has not been assessed.

Therefore, in some embodiments, the disclosed method further comprises assaying the sample from the subject for GFAP, UCH-L1, S-110, inflammatory cytokines, or a combination thereof, in order to increase accuracy of diagnosis and stratification of TBI severity and outcome characterization. Di Battista A P, et al. Front Neurol. 2015 6:110 is incorporated by reference herein for the teaching of these blood biomarkers for TBI and methods for using them to diagnose and stratify TBI. OPN may also be used as part of a panel of other biomarkers to gauge severity, prognosis and guide acute and chronic management of TBI—from concussion to severe coma.

Treatment

The disclosed methods can be used to diagnose a TBI in a subject. Therefore, also disclosed herein is a method of monitoring and/or treating a subject diagnosed by the disclosed methods. It may also be used to monitor the effects of any treatment/s given.

An intraparenchymal intracranial pressure (ICP) sensor can be used for early detection of increased ICP in children with severe TBI. In adults, common practice is to augment arterial blood pressure in instances of raised ICP. In the age groups 2-6, 7-10, and 11-16 years, CPP values of 43, 54, and 58 mmHg, respectively, have been associated with good outcomes.

Sedatives and analgesics can be used for general care of TBI patients to achieve a level of anesthesia needed for invasive procedures, such as airway management, ICP control, to synchronize respiratory efforts with the ventilator, and anxiety relief during diagnostic imaging. Mostly, combination of opioids and benzodiazepines for pain control and sedation are used in children with severe TBI. Neuromuscular blockade can be used in children with severe TBI to improve compliance with mechanical ventilation, reduce metabolic demand, and eliminate shivering.

Intravenous mannitol and hypertonic saline are routinely used to control intracranial hypertension in children with severe TBI. Those osmotic agents are used after or concurrently with sedation, mild hyperventilation, and CSF drainage. Mannitol has been the traditional agent to use and a 20% of mannitol dose of 0.25-1.0 g/kg is often repeatedly administered. Treatment should be titrated to maintain plasma osmolality at 310 mOsm/L. Prevention of hypovolemia is another component of management of TBI. Recently, hypertonic saline has become one of the most popular options to treat intracranial hypertension in the North America.

Cerebrospinal fluid drainage can be used to reduce the volume of the contents of the intracranial vault for the management of increased ICP. An external ventricular drain is commonly used to drain off the CSF. The addition of a lumbar drain may be considered in the case of refractory intracranial hypertension with a functioning external ventricular drainage (EVD), open basal cisterns, and no evidence of a mass lesion or shift on imaging studies. Therapy may be associated with an increased risk of complications from hemorrhage and infection. Therefore, in some embodiments, the disclosed methods are used to select patients for this treatment.

Hyperventilation reduces ICP by lowering CBF by cerebral vasoconstriction of arterioles. Mild hyperventilation ($PaCO_2$, 30-35 mmHg) is recommended in patients who have refractory intracranial hypertension. Under such circumstances, arterial blood gas analysis or end-tidal carbon dioxide ($ETCO_2$) monitoring can be beneficial to monitor and prevent further reducing CBF.

Barbiturates have been considered for the control of refractory intracranial hypertension after other medical therapies have failed. Pentobarbital has been found to be effective in lowering ICP in children with severe TBI.

It is recommended to at least avoid hyperthermia which increases metabolic demands, lipid peroxidation, inflammation, excitotoxicity, and lowering seizure thresholds. Those reactions can cause extensive secondary brain injury. For the use of hypothermia (HT) to treat of refractory intracranial hypertension, the guidelines provide level II evidence for recommending moderate HT to treat severe TBI in children for duration of up to 48 hours following the injury, followed by rewarming slowly to prevent rebound of intracranial hypertension over 12-24 hours. HT is effective in decreasing ICP as an adjunct to standard treatment but, so far, conveyed no functional outcome or increased mortality benefit at 6-months post-TBI.

In pediatric cases, it has been reported that decompressive craniectomy (DC) is performed for controlling intracranial hypertension due to any causes such as TBI, hypoxic-ischemic encephalopathy, metabolic disease, CNS infection, or others, and was effective at ICP reduction. Bifrontal craniotomy is more likely to be selected in children compared to adults. In addition to the mortality, long-term outcome studies are required including the evaluation of various high cognitive functions.

Nutritional support is very important for children with severe TBI. It is recommended that full nutritional replacement be instituted by day 7 post-injury because TBI patients lose sufficient nitrogen to reduce weight by 15% per week and support administration of 130-160% replacement of energy expenditure, which may reduce nitrogen loss.

Children, particularly infants, have lower seizure thresholds and are at high risk for early seizures. Immediate prophylactic administration of anticonvulsant is recommended in children with severe TBI. There is a widespread opinion that prophylactic administration of anticonvulsant is ineffective to prevent the development of epilepsy. Risk factors for early onset of seizures in infants aged less than 2 years include concomitant hypotension, history of child abuse, and Glasgow Coma Scale score of ≤8. In such cases, prophylactic anticonvulsant is recommended. No specific guidelines exist for the discontinuation of prophylactic anticonvulsant. If no further seizures occur more than 2 years after the last seizure, imaging studies, electroencephalogram (EEG), and CBF studies are recommended to decide potential reduction in dosage by half.

Kits

Also disclosed herein is an article of manufacture comprising packaging material and an anti-Osteopontin antibody suitable for an ELISA assay. The kit can further contain antibodies that selectively bind GFAP, UCH-L1, S-110, inflammatory cytokines, or a combination thereof. The kit can further contain loading control antibodies, such as anti-actin antibodies. The kit can further contain standards for creating a standard curve, e.g. OPN protein at a set concentration. The packaging material can comprise a label or package insert which indicates how the antibodies can be used to diagnose traumatic brain injury.

Furthermore, the kit preferably comprises instructions for interpreting the results of the OPN concentration, and optionally the at least one further biomarker concentration, with respect to providing a diagnosis, prognosis and/or risk stratification of the subject whose biological sample was analyzed, such as for identifying patients or patient subgroups with elevated OPN concentrations, which suffer from a significantly higher cardiac risk. For example, the packaging material can also contain OPN reference values, such as the OPN cut-off value.

A number of embodiments of the disclosure have been described. Nevertheless, it will be understood that various modifications may be made without departing from the spirit and scope of the disclosure. Accordingly, other embodiments are within the scope of the following claims.

EXAMPLES

Example 1: Plasma Osteopontin May Predict Neuroinflammation and the Severity of Pediatric Traumatic Brain Injury Materials and Methods Controlled cortical impact model (CCI) for traumatic brain injury CCI model was established in juvenile (4-week-old) male C57BL/6 or CX3CR1GFP/+ mice using an electromagenetic device (Impact One, Leica Biosystems) (Osier N D, et al. Front Neurol 2016 7:134). Briefly, the mouse was anesthetized by 2% isoflurane and the body temperature was maintained at 37° C. during surgery. A central incision was made to expose the skull. In the center of Lambda and Bregma, a circular craniotomy with 4 mm diameter and 0.5 mm away from the midline was made on left side of brain to expose the intact dura. The CCI parameters were velocity at 3 m/s, compression time at 500 ms, and deformation depth at 2 mm. The blood following impact was cleaned and the wound was closed with tissue glue. For shams, craniotomy was made with an intact dura. The mouse temperature was maintained at 37° C. after surgery until recovery from anesthesia. After CCI, mice were examined daily and assessed for the neurological severity score (NSS) (Shapira Y, et al. Crit Care Med 1988 16:258-265). In this scoring system, inability to exit from a circle of 50 cm in diameter when placed in the center for 30 min, loss of righting reflex when left on its back, loss of seeking behavior, and hemiplegia or hemiparesis was each scored for one point. NSS≤2 at 48 hours post-CCI was classified as low-NSS. NSS 3-4 was classified as high-NSS. All procedures were approved by the Institutional Animal Care and Use Committee (IACUC) and the National Institutes of Health Guide for Care and Use of Laboratory Animals.

Human Study Population

Subjects were patients between the ages of 0 and 18 years-old, who were brought to the Emergency Department (ED) at Children's Healthcare of Atlanta (CHOA) Scottish Rite and Egleston hospitals with a diagnosis of TBI made by a medical professional. All levels of Glasgow Coma Score (GCS) were eligible, and patients were classified as mild TBI (GCS 13-15), moderate TBI (9-12), or severe TBI (GCS 3-8). Exclusion criteria were children outside the age parameters or had a non-traumatic head injury or other type of medical illness. The protocol was approved by the Institutional Review Board (IRB) at CHOA. Informed consent was obtained from parents.

Immunoflorescence Staining and Immunoblotting Analysis

The following antibodies and working dilution were used in immunofluorescence staining: goat anti-OPN (1:100, R&D), anti-goat 588 (1:500, Biolegend), rat anti-F4/80 (1:100, Bio-Rad), biotinylated rat IgG (1:250, Biolegend), Alexa fluor 647 streptavidin (1:500 Biolegend). The following antibodies and working dilution were used in immunoblotting: goat anti-OPN (1:1000, R&D), goat anti-MMP9 (1:1000, Sigma), rabbit anti-GFAP (1:10000, Abcam), rabbit anti-actin (1:10000, Sigma), rabbit anti-transferrin (1:10000, Sigma). 0.2 μg of mouse recombinant OPN (R&D) was used in immunoblots as positive control.

Luminex Assay in Mice

Mouse plasma was collected using heparin as an anticoagulant, then centrifuged for 20 minutes at 1000×g at 2-8° C. within 30 minutes of collection. The plasma was diluted 50 times with the buffer in luminex kit (R&D). The luminex bead-based ELISA was assayed and analyzed using a Bio-Plex system (Bio-Rad).

ELISA Assay of Plasma OPN and GFAP

Human plasma was diluted properly and OPN and GFAP level were analyzed in duplicate for each sample using commercial ELISA kits (R&D). Any samples not in calibrator range were re-diluted and assayed again.

Statistical Analysis

All data was analyzed using the GraphPad prism 7 analytical software. Levels of OPN or GFAP between two groups were compared using the Mann-Whitney test, and p-value <0.05 was considered statistically significant. Correlation of OPN or GFAP with short-term outcomes (the onventilator days and in-ICU days) were analyzed using Spearman's rank correlation test. Prognostic value of OPN or GFAP were analyzed using the receiver operating characteristic (ROC) curve, as previously described (Swets J A. Science 1988 240:1285-1293). A p-value <0.05 and AUC of 0.7-0.8 was valued as adequate accuracy in diagnosis.

Results

Figure 1B:
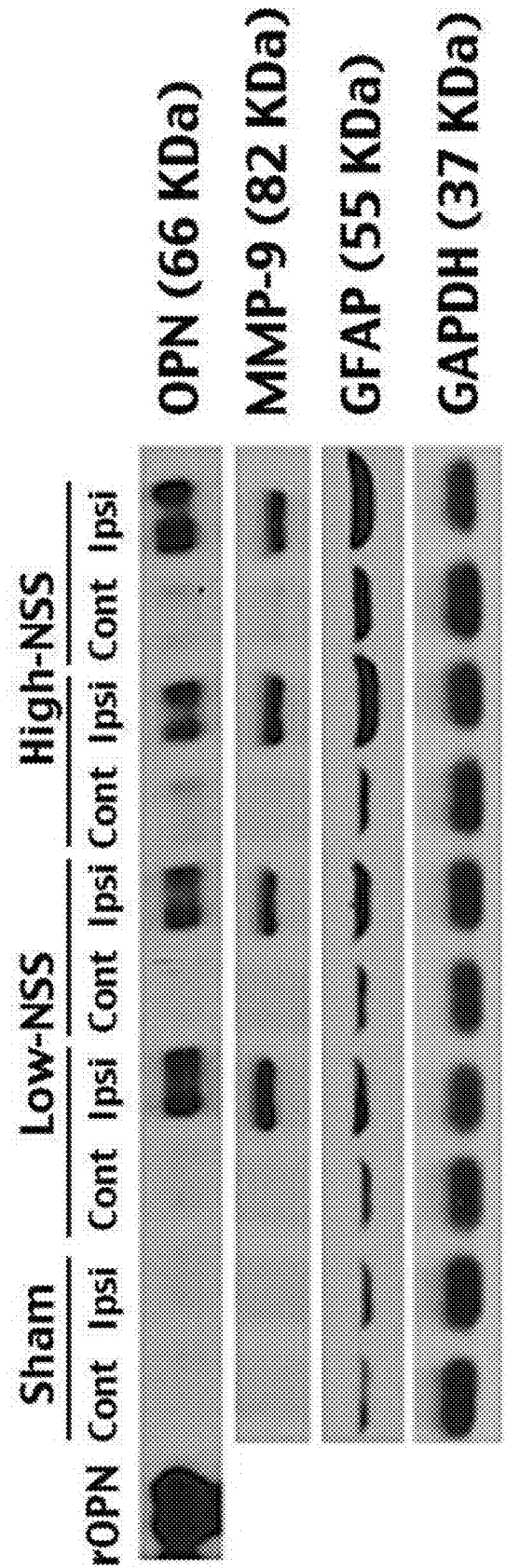
Figure 1C:
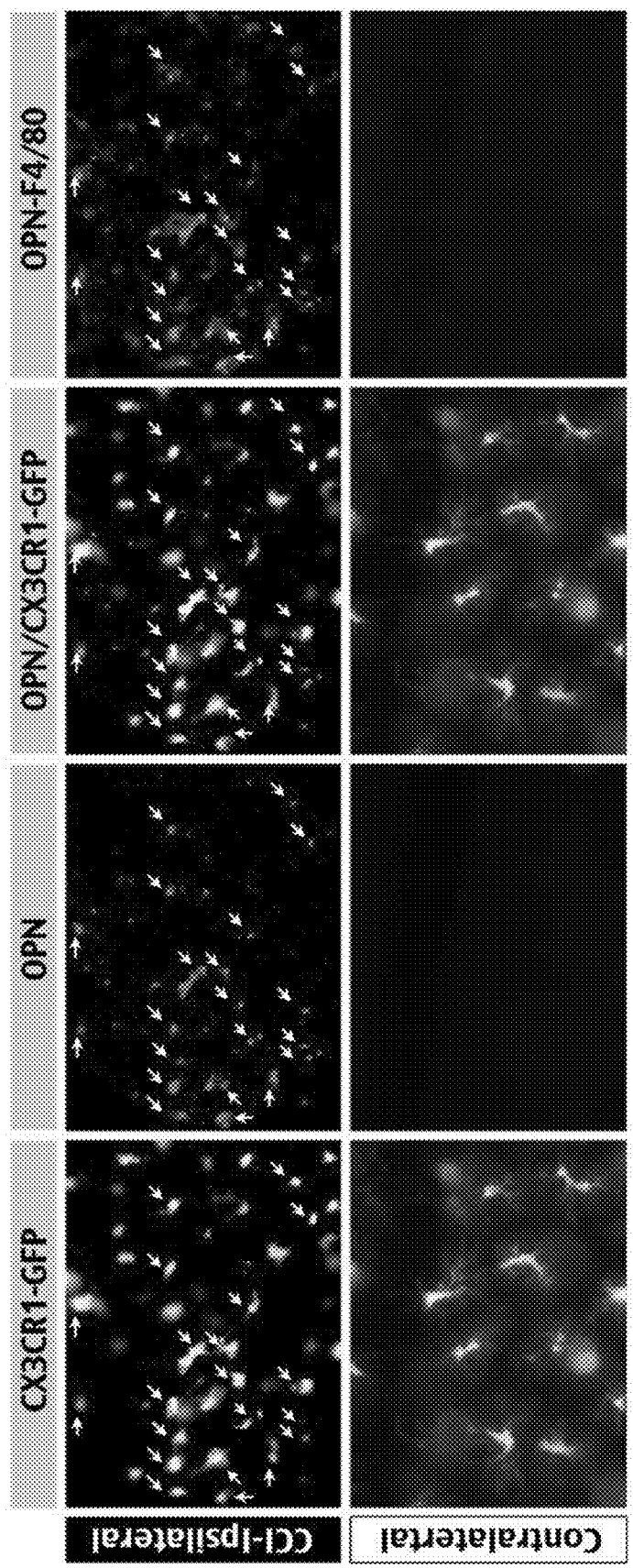
Figure 1D:
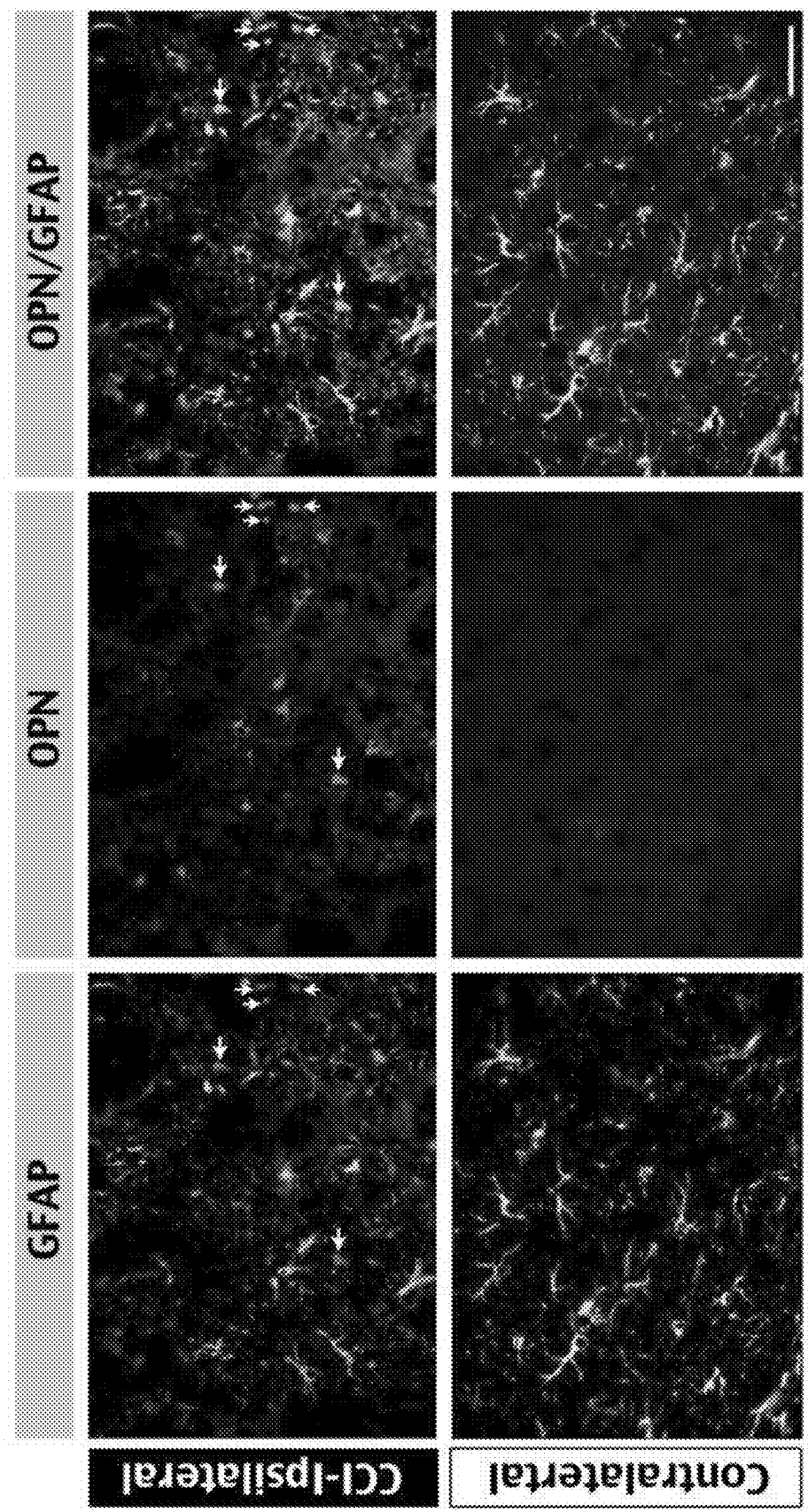

OPN, GFAP, and MMP-9 levels were compared in the brain and blood in the controlled cortical impact (CCI) model to examine the possibility of OPN induction after TBI. CCI was first applied to one-month-old male CX3CR1GFP/+ mice, in which microglia and monocytes/macrophages are tagged by the green fluorescence protein (GFP) (Osier N D, et al. Front Neurol 2016 7:134). Immunoblot indicated marked induction of OPN and MMP-9, and to a lesser degree GFAP, in the ipsilateral hemisphere of CCI-injured mice that exhibited either a low (≤2) or high (3-4) neurologic severity score (NSS) at 48 hours of recovery (Shapira Y, et al. Crit Care Med 1988 16:258-265). Importantly, there was no induction of OPN or MMP-9 in the contralateral hemisphere (FIG. 1B, n>6 in each group). Similarly, immunostaining showed selective induction of OPN in the ipsilateral, but not contralateral hemisphere in CCI-injured CX3CR1GFP/+ mice (FIG. 1C, 1D; n>3). Further, the anti-OPN immunosignals were predominantly localized in GFP and F4/80 double-positive activated microglia/macrophages rather than GFAP-positive astrocytes (arrows in FIG. 1C, 1D). These data suggest that the brain OPN and MMP-9 and GFAP up-regulation are all markers for CCI in juvenile mice.

Figure 2A:
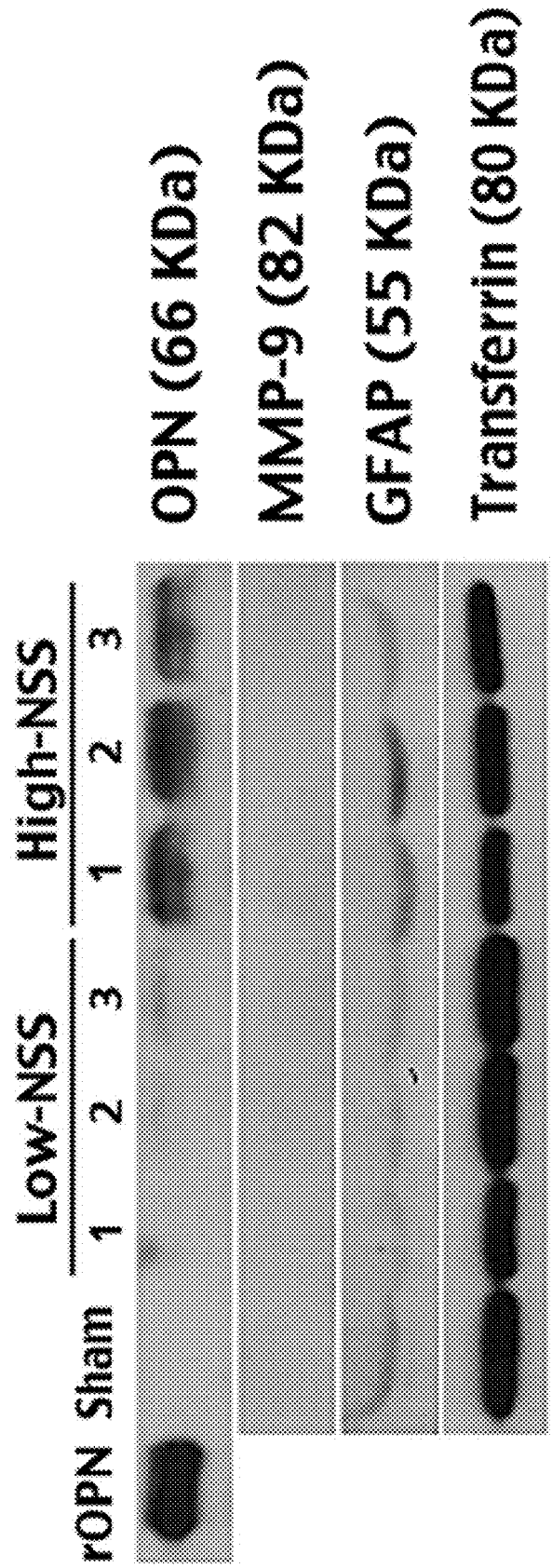
FIGS. 2A to 2C show induction of the plasma OPN and GFAP after CCI in juvenile mice.
Figure 2B:
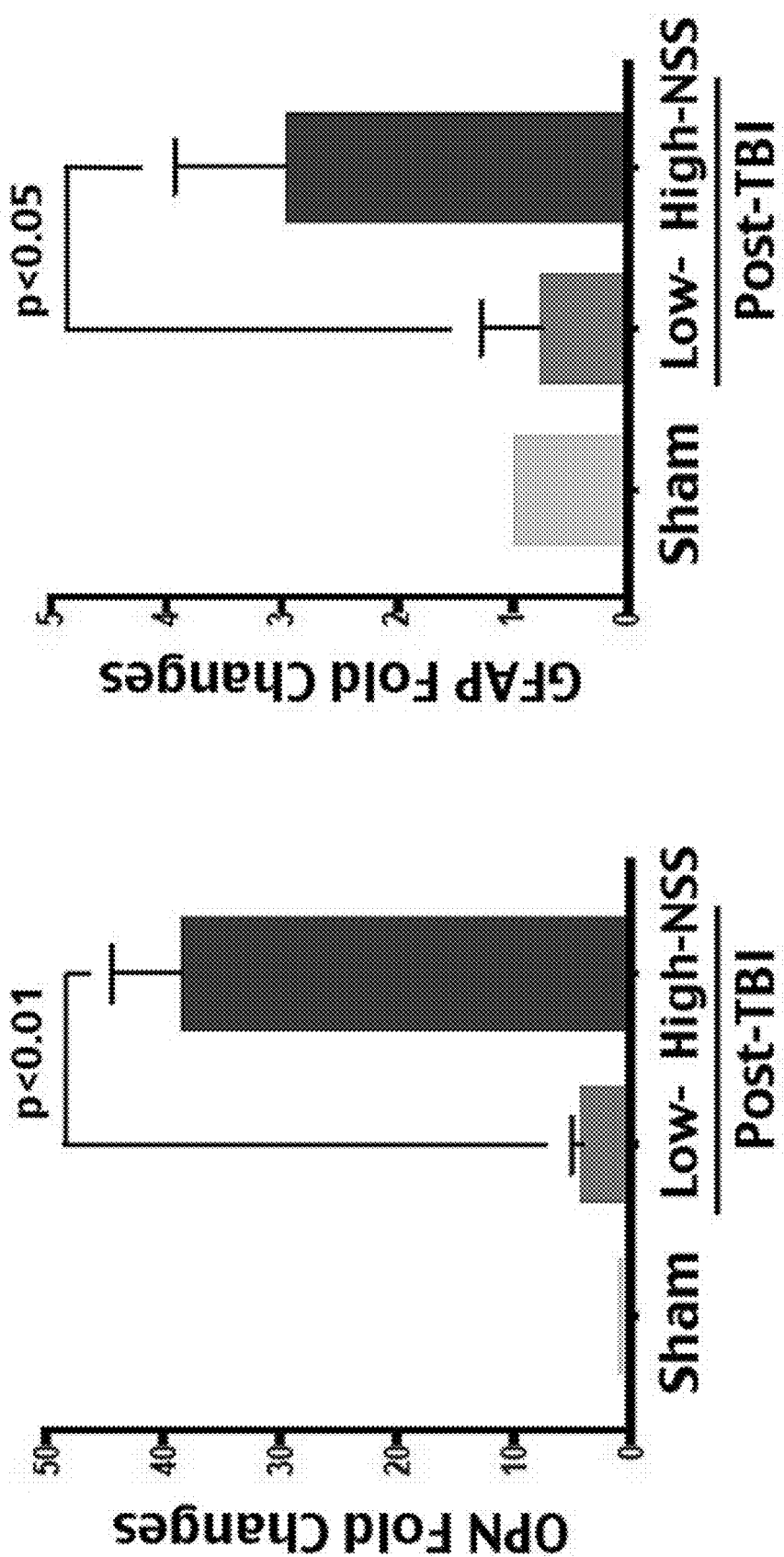
Figure 2C:
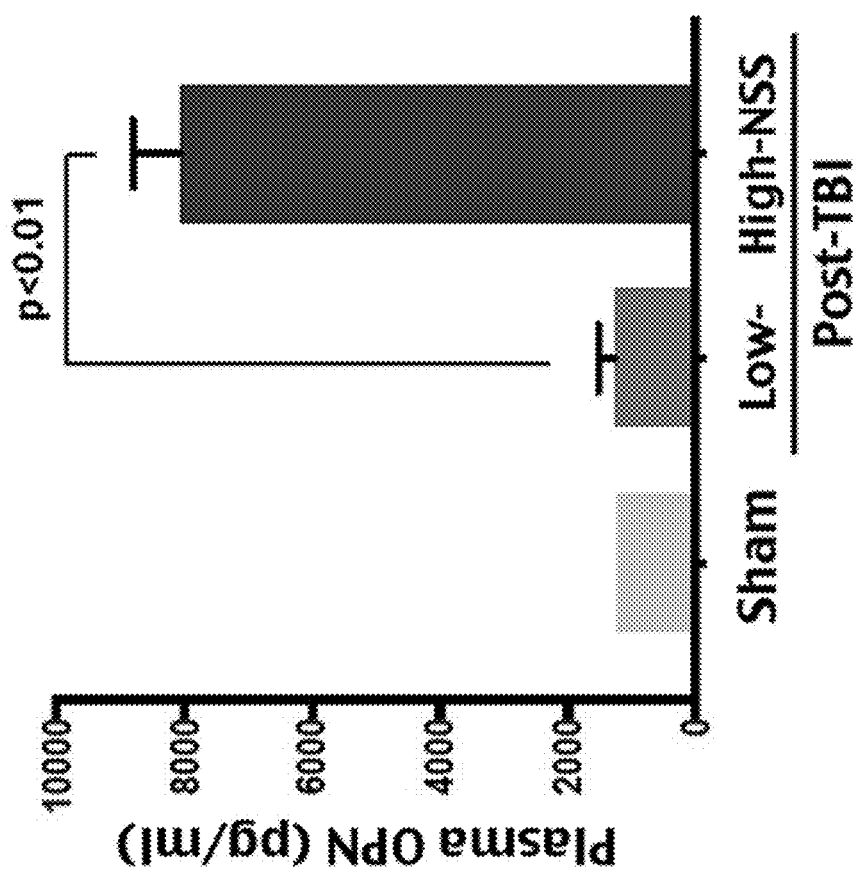

However, immunoblot using the plasma from this CX3CR1GFP/+ mouse cohort only detected induction of OPN and GFAP, but not MMP-9, at 48 hours post-CCI (FIG. 2A, n>6 in each group). Moreover, immublot quantification revealed significantly greater induction of OPN (p<0.01) and GFAP (p<0.05) in the CCI-injured mice with high-rather than low-NSS (FIG. 2B, n=3). This pattern of specific plasma OPN induction in mice manifesting high NSS after CCI was also corroborated by enzyme-linked immunosorbent assay (FIG. 2C). These preclinical results suggest that induction of plasma OPN may signify severe TBI and/or worse outcomes in children.

Comparison of Plasma OPN and GFAP in the Acute Phase of Pediatric TBI

Figure 3A:
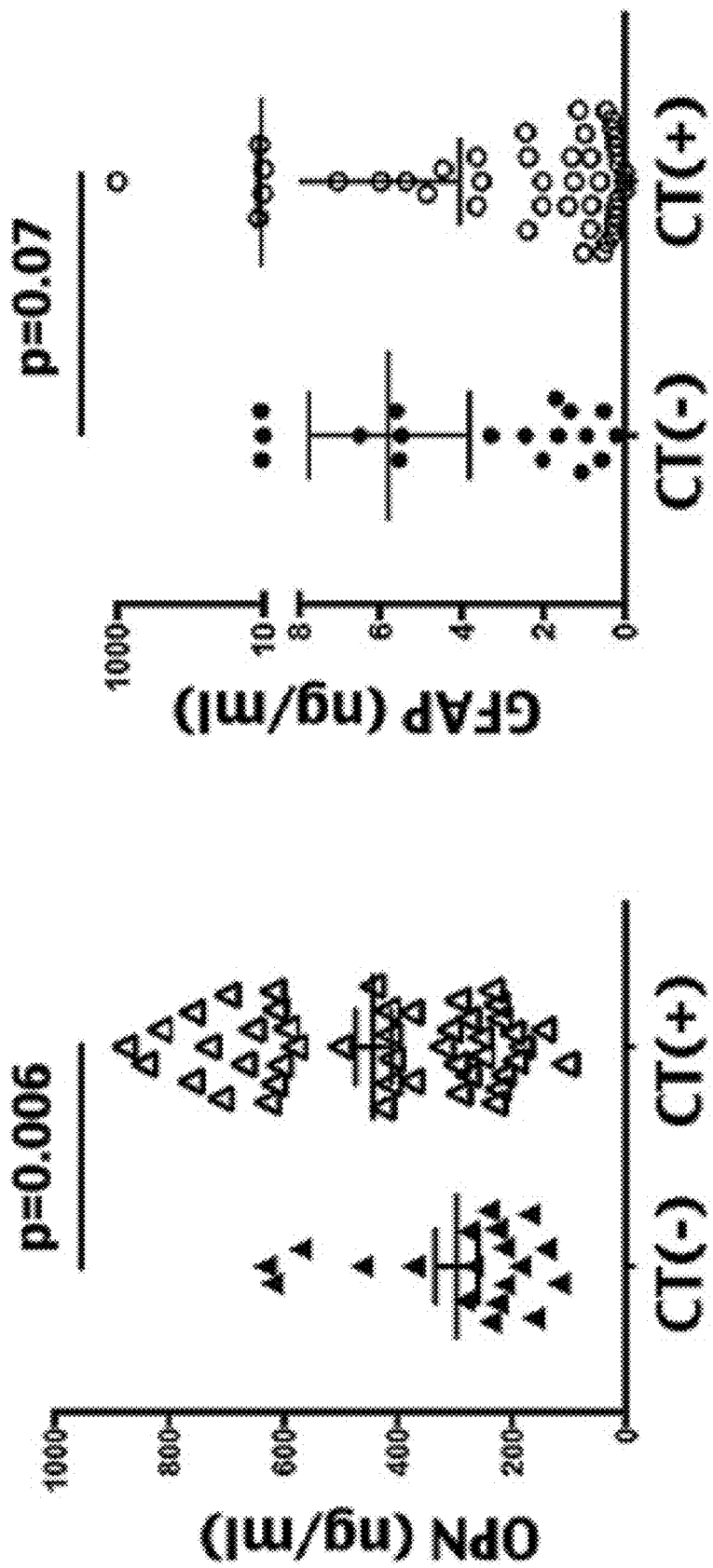
FIGS. 3A and 3B shows prediction of pediatric severe TBI using the plasma OPN and GFAP levels at admission.
Figure 3B:
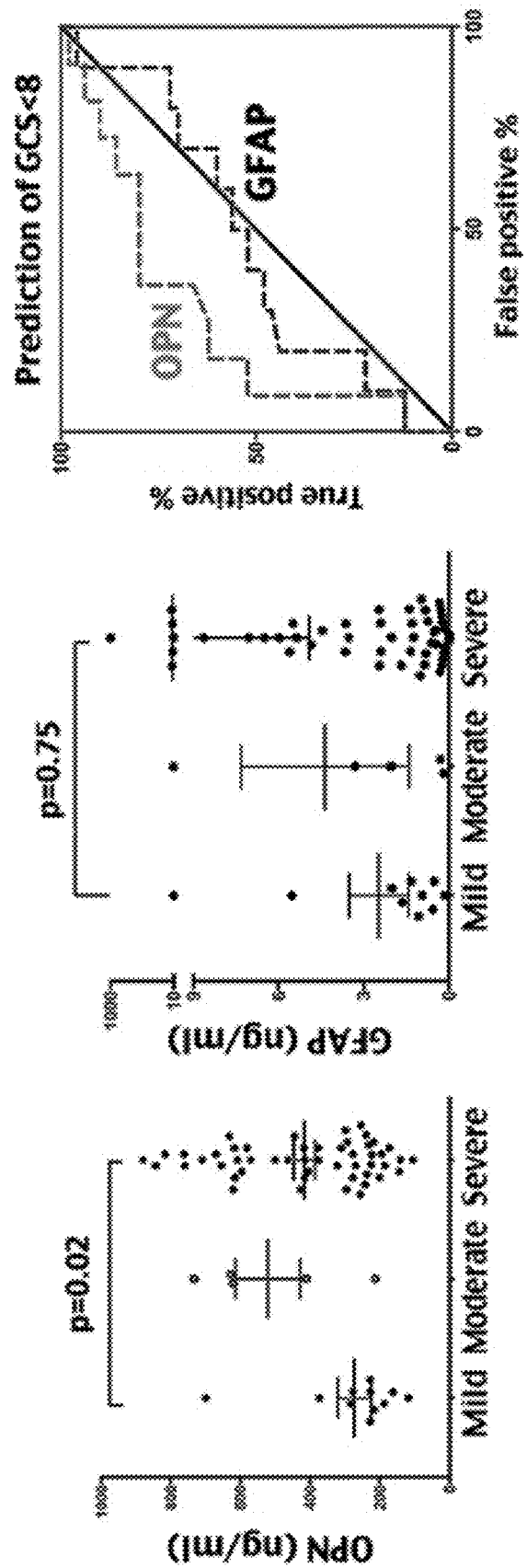

To begin to test this hypothesis, the plasma OPN and GFAP levels were compared in 66 TBI-injured children with and without CT-evidence of intracranial lesions at admission. The cohort included 50 severe TBI (GCS: 3-8; 7.3±0.7 years of age), 5 moderate TBI (GCS: 9-12; aged 5.9±3.1 years), and 11 mild TBI cases (GCS: 13-15; aged 7.2±1.4 years) (Table 1). This analysis showed that the initial at-admission plasma levels of OPN were significantly higher in children with intracranial lesions (n=46, one severe TBI case did not receive CT scan) than those with negative CT findings (n=19) (FIG. 3A, p=0.006 by t-test). In contrast, the initial plasma GFAP levels were comparable in those with and without CT evidence of intracranial lesions at admission (p=0.07), consistent with the finding in a recent report (Mondello S, et al. Science Report 2016 6:28203). Moreover, the initial plasma OPN levels were higher in children with severe TBI than those with mild TBI (FIG. 3B, p=0.02 by t-test), whereas the difference of plasma GFAP levels between the severe- and mild-TBI groups were not significant (p=0.75). The Receiver Operating Characteristic (ROC) graph analysis also indicated a higher accuracy of using the initial plasma OPN levels to predict severe TBI (GCS: 3-8) at admission compared with the plasma GFAP levels (FIG. 3B). These data suggest that plasma OPN is a better diagnostic biomarker than GFAP in the acute phase of pediatric TBI.

TABLE 1

Demographic and clinical characteristics of the study population

| Characteristics | TBI patients (n = 66) | | |
| --- | --- | --- | --- |
| | Severe TBI (GCS 3-8) n = 50 | Moderate TBI (GCS 9-12) n = 5 | Mild TBI (GCS 13-15) n = 11 |
| Ages, years | 7.26 ± 0.74 | 5.9 ± 3.11 | 7.18 ± 1.4 |
| Sex, n (%) | | | |
| Male | 31 (62%) | 4 (80%) | 6 (55%) |
| Female | 19 (38%) | 1 (20%) | 5 (45%) |
| Race, n (%) | | | |
| Africa America | 23 (46%) | 4 (80%) | 4 (36%) |
| Caucasian | 20 (40%) | — | 7 (64%) |
| White | 2 (4%) | — | — |
| Asian | 2 (4%) | 1 (20%) | — |
| Unknown | 3 (6%) | | |
| Cause of injury, n (%) | | | |
| Road traffic incidence | 21 (42%) | — | 5 (46%) |
| Incidental fall | 15 (30%) | 1 (20%) | 2 (18%) |
| Violence/Assault | 3 (6%) | — | — |
| Gun shot | 3 (6%) | 1 (20%) | — |
| Sports related injury | 1 (2%) | 2 (40%) | 1 (9%) |
| Other nonintentional injury | 3 (6%) | — | 2 (18%) |
| Other/unknown | 4 (8%) | 1 (20%) | 1 (9%) |
| CT-Imaging, n (%) | | | |
| Intracranial lesion On head CT | 40 (80%) | 4 (80%) | 2 (18%) |
| Skull Fracture Only | 3 (6%) | — | 2 (18%) |
| Negative CT | 6 (12%) | 1 (20%) | 7 (64%) |
| Deceased, n | 5 | — | — |

Figure 4A:
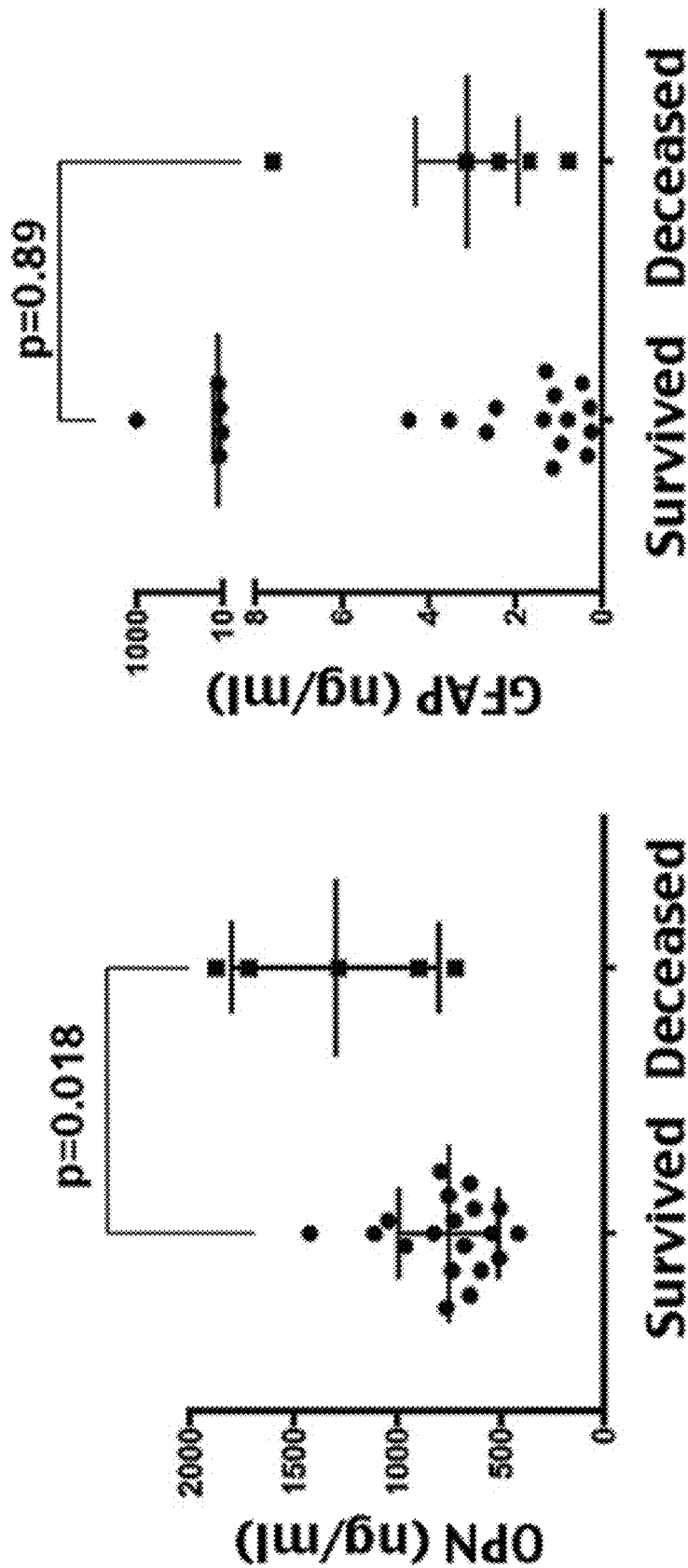
FIGS. 4A to 4C show correlation of the peak plasma OPN and GFAP levels within 72 hours of hospitalization with mortality and the length of ventilator or intensive care in children with severe TBI.

Correlation of clinical course with the peak plasma OPN and GFAP levels within 72 hours of TBI Serial blood samples (at admission, 24, 48, and 72 hours of hospitalization) were obtained in 24 severe TBI patients in the cohort, five of which later deceased. A trend of rising plasma OPN levels was noted in these serial blood samples, and interestingly, although the plasma OPN levels of those later deceased were similar to those survived at admission, 24, and 48 hours, they were significantly higher at 72 hours of hospitalization (FIG. 4A, p=0.018 by t-test). In contrast, the plasma GFAP levels in severe TBI patients that later deceased were inseparable from those that survived from admission to 72 hours of hospitalization (p=0.89 by t-test). These data suggest that the trajectory of plasma OPN levels in pediatric TBI may predict the clinical course or outcomes.

Figure 4B:
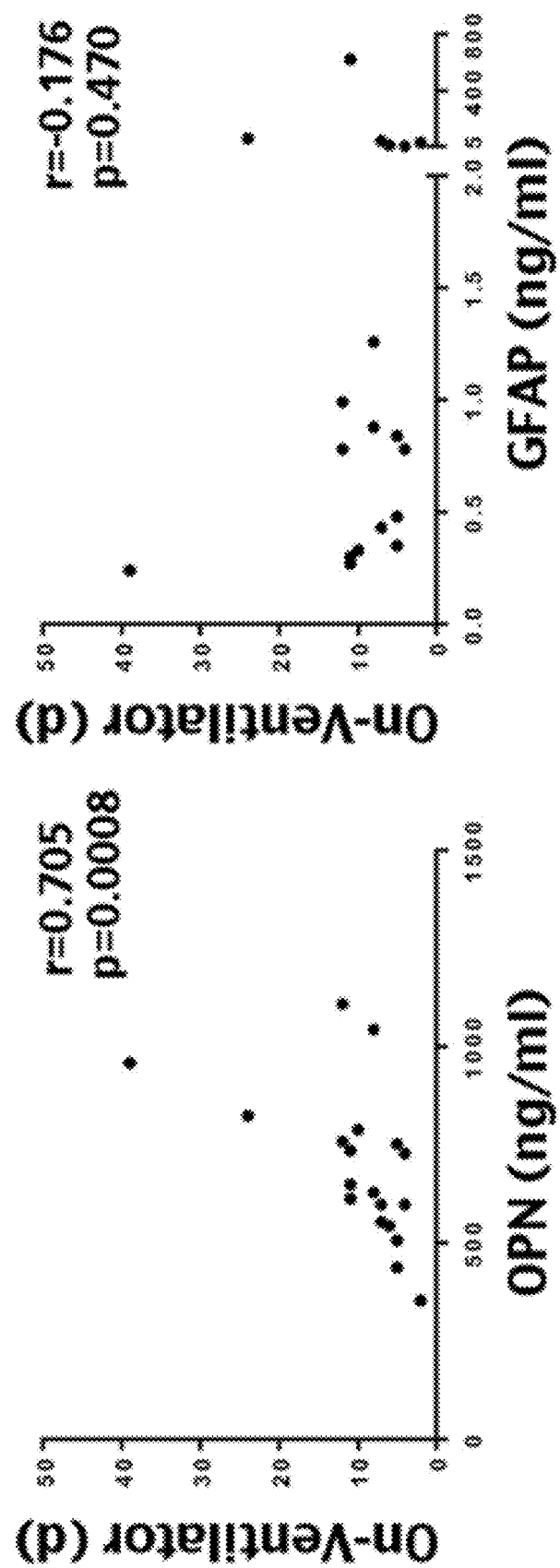
Figure 4C:
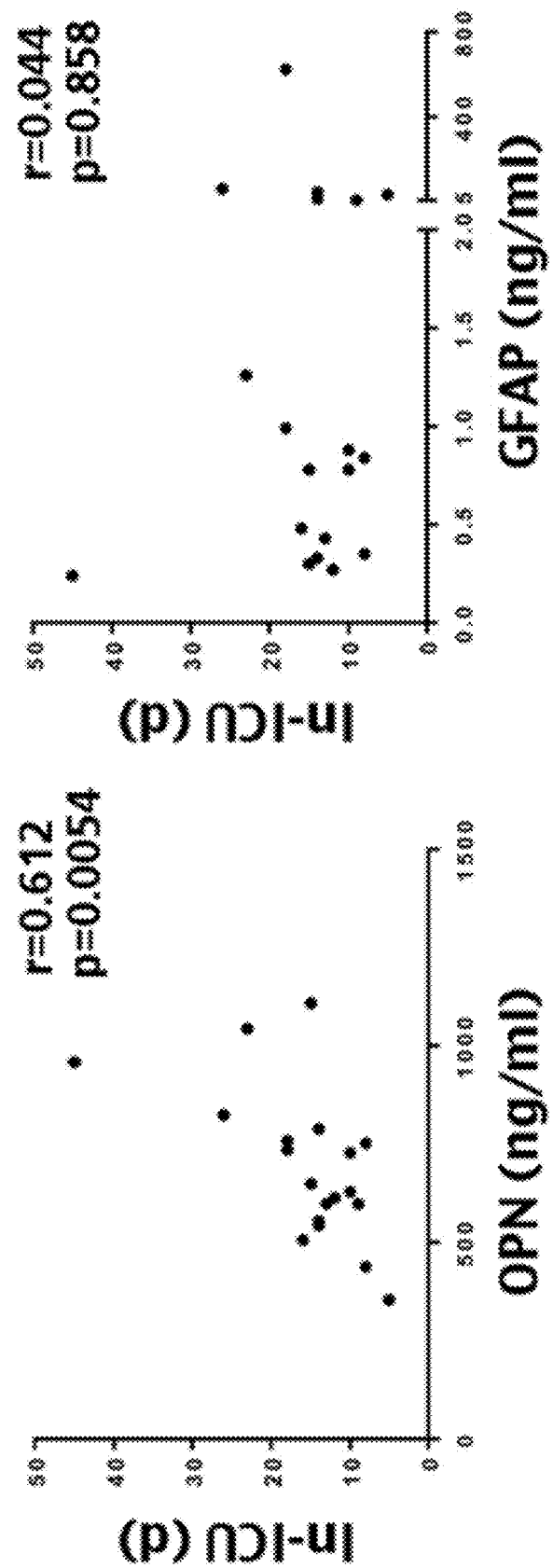

To examine this possibility, the highest plasma OPN and GFAP levels were plotted within 72 hours of admission against the days of ventilator or intensive care unit (ICU) support in hospitalization, as two objective short-term outcome measurements, in 19 severe TBI-injured children (the 5 cases that later deceased were excluded). This analysis indicated correlation between the peak plasma OPN levels and the duration of ventilator or ICU support. The Spearman's rank coefficient (r) between the peak plasma OPN levels and on-ventilator days was 0.7049 (FIG. 4B, p=0.0008), and 0.6112 with the in-ICU days (FIG. 4C, p=0.0054). In contrast, no significant correlation was identified?? between the peak plasma GFAP levels and the days requiring the ventilator or ICU support (p=0.4699 and p=0.8579, respectively). Hence, OPN outperforms GFAP as a blood biomarker to predict short-term outcomes in this cohort of pediatric severe TBI patients.

Discussion

Current management of TBI solely relies on radiographic imaging and neurological examinations to predict the severity and monitor the progression of brain damage. Blood-based biomarker tests that correlate with clinical severity and evolution of TBI brain damage would enable appropriate triage in acute treatment, early intervention of complications, and follow-up rehabilitation planning (Au A K, et al. Curr Opin Neurol 2017 30:565-572; Adrian H, et al. eNeuro 2016 e0294-16 2016 1-13). The need to develop TBI blood biomarkers is particularly urgent in children, because the highest rates of TBI-related emergency department visits by age-group fall in 0-4, 5-14, and 15-24 years, which are 2-4 fold higher than the incidence in the 25-44 years group. In addition, the blood biomarkers with proven utility in adult TBI, such as GFAP, may not be applicable in the pediatric population (Okonkwo D O, et al. J Neurotrauma 2013 30:1490-1497; Mondello S, et al. Science Report 2016 6:28203).

In view of a far-reaching scope of neuroinflammation after TBI, proteins that are produced by activated microglia/macrophages and possessing high brain-to-blood transport efficiency, as well as, stability in body fluids may be useful blood biomarkers in pediatric TBI. In particular, OPN is disclosed herein for this purpose owing to its several unique attributes. First, the baseline level of brain OPN is negligible, but it is rapidly increased by activated microglia and macrophages in a multitude of neurological conditions, including neonatal hypoxia-ischemia, stroke, electrolytic lesion, TBI, and Alzheimer's models, although the functions of OPN in brain damage remain partially understood (Ellison J A, et al. Stroke 1998 29:1698-1706; Chen W, et al. Stroke 2011 42:764-769; van Velthoven C T, et al. Stroke 2011 42:2294-2301; Li Y, et al. eNeuro 2017 4(1). pii: ENEURO.0253-16.2016; Chan J L, et al. Exp Neurol 2014 261:757-771; von Gertten C, et al. BMC Neurosci 2005 6:69; Rentsendorj A, et al. Brain Behav Immun 2017 67:163-180). Second, perhaps due to its integrin-binding property, OPN exhibits high brain-to-blood transport efficiency and great stability in the blood and saliva (Bellahcene A, et al. Nature Reviews Cancer 2008 8:212-226; Lanteri P, et al. Clin Chem Lab Med 2012 50:1979-1984; Gopal N, et al. J Clin Diagn Res 2016 10:BC06-08; Li Y, et al. eNeuro 2017 4(1). pii: ENEURO.0253-16.2016). In experimental hypoxic-ischemic injury of newborns, it has been demonstrated the increased plasma OPN was derived from microglia and correlated with the severity of brain damage (Li Y, et al. eNeuro 2017 4(1). pii: ENEURO.0253-16.2016). Third, perhaps except for head trauma in the shaken baby syndrome, the majority of pediatric TBI patients enjoy healthy brains prior to the accident, which may decrease the baseline level of plasma OPN. Finally, there is a greater than tenfold increase of OPN in cerebrospinal fluid (CSF) correlated with clinical severity in acute TBI patients, when compared to controls (Antonios A, et al. 3rd International Conference on Neurological Disorders and Brain Injury 2017).

The disclosed translational study provides two set of experimental data (both preclinical and clinical). In preclinical experiments, it was shown that the brain OPN and MMP-9, and GFAP are sensitive biomarkers of traumatic brain damage in juvenile mice (FIG. 1). However, only OPN and GFAP, but not MMP-9, increase in blood and correlate with high neurological severity score. Interestingly, plasma OPN exhibit greater induction than plasma GFAP in TBI-injured juvenile mice, suggesting that OPN may be a more sensitive or specific blood biomarker in pediatric TBI (FIG. 2). Indeed, using the archived plasma proteins from 66 children brought to emergency service due to TBI, the initial plasma OPN level was shown to be a better diagnostic biomarker of severe TBI (GCS 8) and CT-evidenced intracranial lesion than GFAP (FIG. 3). Moreover, the peak plasma level of OPN within 72 hours of TBI onset is superior to that of GFAP in correlation with mortality and the length of ventilator or ICU support in hospitalization in children with severe pediatric TBI (FIG. 4). These results suggest that OPN is a valuable blood-based biomarker to assist the diagnosis and outcome predictions in pediatric TBI.

In conclusion, the merits of OPN as a blood biomarker in pediatric TBI may arise from its strong induction in microglia/macrophages during neuroinflammation plus highly efficient transport and stability in the biofluids. With these unique attributes, OPN is a promising blood biomarker in pediatric TBI.

Example 2: Plasma Osteopontin Levels is a Putative Biomarker for Abusive Head Trauma in Children Objective Although Abusive Head Trauma (AHT) in children is associated with significant morbidity and mortality, it is significantly understudied. Further, these cases are a diagnostic challenge, especially given potentially dire consequences of returning these children to a persistent hostile environment. Thus, there is an urgent, unmet need to quickly, specifically and objectively make the diagnosis of AHT. To date, there are no biomarkers that are sufficiently sensitive to detect abusive head injury, to determine the recovery trajectory, and aid in developing plans for management. This study aims to evaluate the ability of OPN levels to distinguish between AHT from other mechanisms of TBI. The study additionally explores the relationship between AHT and rehabilitation outcomes.

Participants 79 pediatric TBI patients (ages 0-4); 24 confirmed AHT and 55 accidental trauma. Of these, 59 completed inpatient rehabilitation. Blood was drawn within 6 hours of admission and at 24 hour, 48 hour and 72 hours in order to measure for OPN levels. WeeFIM ratings were collected at admission and discharge from inpatient rehabilitation.

Results

Mean values for OPN over time is shown in FIG. 5 and Table 2. No differences in Glasgow coma score (GCS) across groups (6.25 vs. 6.56). AHT group was younger (mean age 0.65 vs. 2.36 years). Higher OPN levels found in AHT at admission (p=0.008) and 72 hours (p=0.044) compared to accidental trauma group. AHT group showed less improvement (mean WeeFIM change 4.73 vs. 18.48) during inpatient rehabilitation as measured by WeeFIM scores (t(30)=2.406, p=0.02).

TABLE 2

Patient Medical Characteristics

| | All (N = 79) | AHT (N = 24) | Accidental Trauma (N = 55) | P-value |
|---|---|---|---|---|
| GCS | 5 (3-8) | 6.25 | 6.56 | 0.524 |
| Deceased | 17 (22%) | 9 (38%) | 8 (15%) | 0.022 |
| Severity | | | | 0.208 |
| Mild Complicated | 12 (15%) | 5 (21%) | 7 (13%) | |
| Moderate | 6 (8%) | 0 | 6 (11%) | |
| Severe | 61 (77%) | 19 (79%) | 42 (76%) | |
| LOS, days | 7 (3-14) | 11 (6-20) | 5 (2-12) | 0.020 |
| Vent days | 3 (1-10) | 8 (3-11.5) | 3 (1-8) | 0.020 |
| Craniotomy | 22 (28%) | 8 (33%) | 14 (25%) | 0.473 |
| Skull Fracture | 45 (58%) | 10 (42%) | 35 (65%) | 0.056 |
| Rehabilitation | 32 (41%) | 11 (46%) | 21 (38%) | 0.524 |
| Intubated | 67 (84.8%) | 21 (88%) | 46 (84%) | 0.747 |
| Sedated | 38 (48%) | 29 (53%) | 9 (38%) | 0.213 |
| EVD | 31 (39%) | 12 (50%) | 19 (35%) | 0.196 |
| OPN Available[1] | | | | |
| ADM, n = 78 | 313.8 (232.9-604.9) | 471.5 (332.3-637.8) | 280.2 (191-504.7) | 0.008 |
| 24 h, n = 35 | 534.8 (404.4-697.0) | 633.5 (433-791) | 507.3 (379.9-673.0) | 0.242 |
| 48 h, n = 27 | 613 (273.5-778.7) | 720 (616.0-893.0) | 462.0 (241.6-687.7) | 0.141 |
| 762 h, n = 18 | 697.5 (522.2-1283) | 1114.5 (1002.2-1717) | 606.9 (218.9-768.4) | 0.044 |

P-value: Wilcoxon Rank-sum tests for continuous variables of Chi-squared (if cell count <5, Fisher's Exact) test for categorical variables. Statistical significance assessed at the 0.05 level.
P < 0.05 shown in bold.
[1]Missing values: OPN at admission, n = 1 missing; at 24 hours, n = 44 missing; at 48 hours, n = 52 missing; at 72 hours, n = 61 missing.

Conclusions

OPN may serve as an objective indicator to support a diagnosis of abusive head trauma. Additionally, a more accurate diagnosis of AHT could help physiatrists to better anticipate recovery patterns and inform treatment decisions among survivors.

Example 3: Use of Serum Osteopontin Levels as a Biomarker for TBI in Adults

Figure 6A:
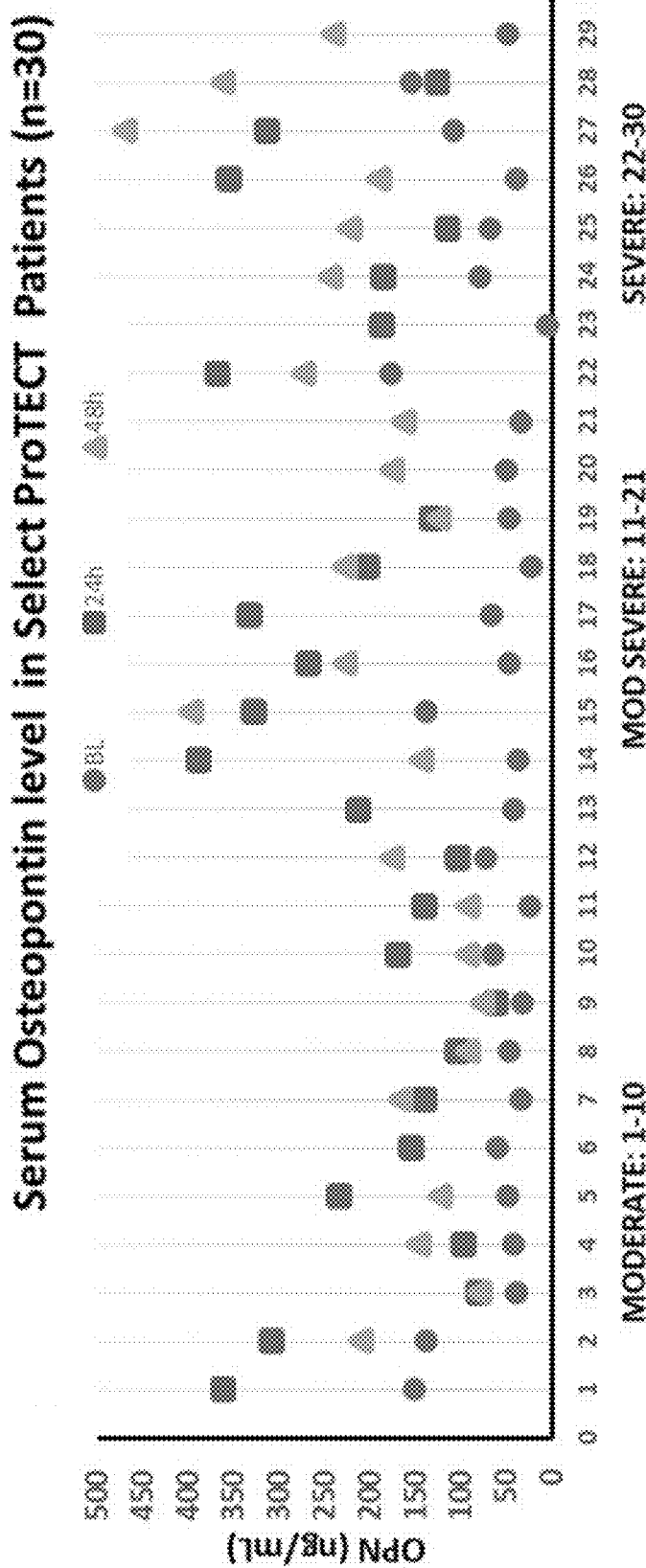
FIGS. 6A and 6B show serum levels of OPN, within 48 h of TBI onset.
Figure 6B:
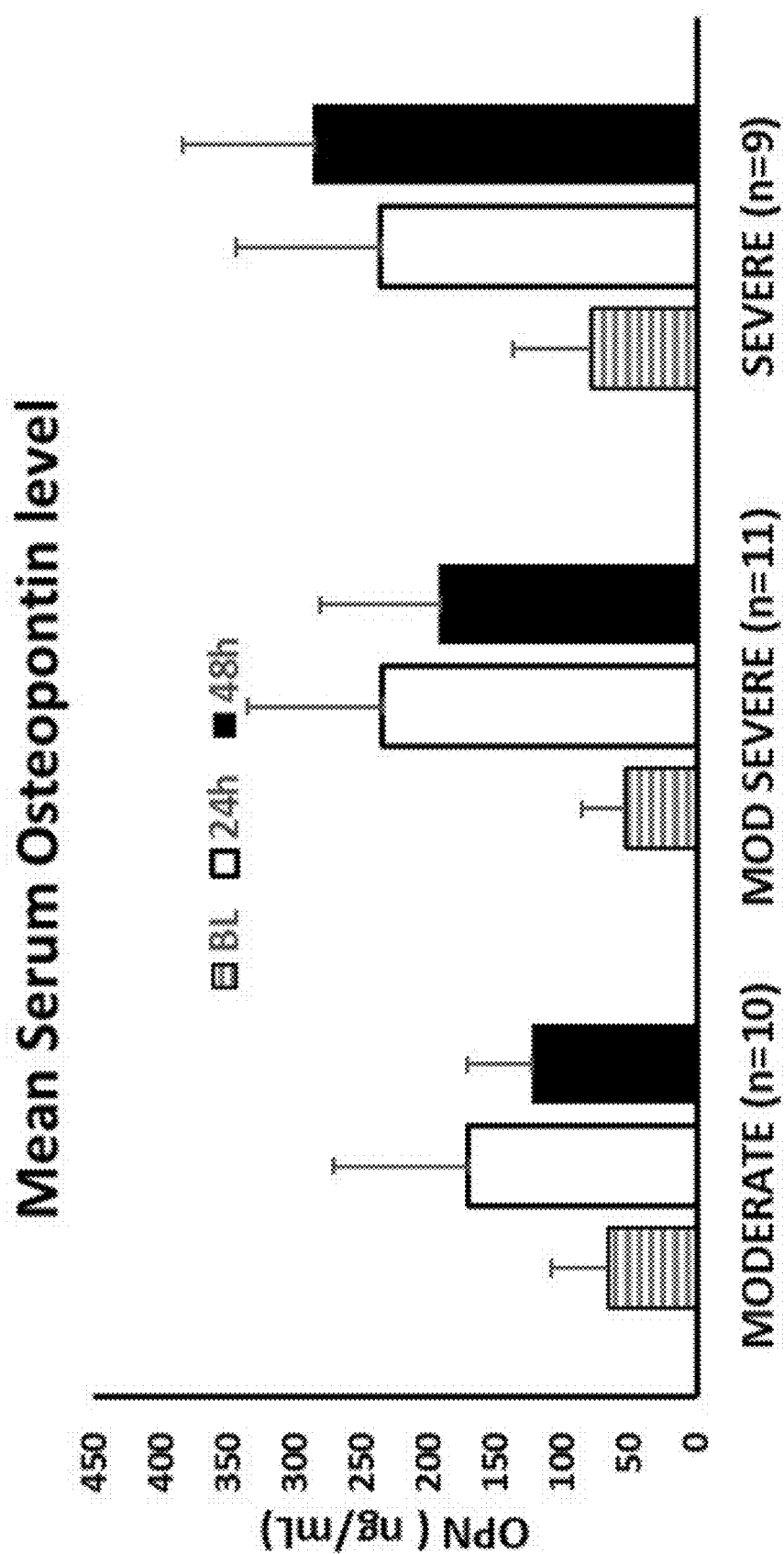

Serum OPN levels in subset of moderate to severe TBI patients enrolled in ProTECT III: Serum OPN levels were compared in 30 enrolled patients with moderate (n=10), moderate-severe (n=11), or severe TBI (n=9). At 24 and 48 h post-TBI there was an increase in OPN levels in the moderate-severe and severe groups compared to the moderate group (FIGS. 6A and 6B). Initial serum OPN levels (65.70±45.00) were also observed to be higher than the reported mean plasma OPN (23.56±19.73 ng/mL) level of healthy subjects.

In summary, the results of this study can be taken to suggest that OPN may be a useful blood biomarker to predict severity, clinical course, and functional outcomes in TBI patients even when complicated by multi-trauma.

Unless defined otherwise, all technical and scientific terms used herein have the same meanings as commonly understood by one of skill in the art to which the disclosed disclosure belongs. Publications cited herein and the materials for which they are cited are specifically incorporated by reference.

Those skilled in the art will recognize, or be able to ascertain using no more than routine experimentation, many equivalents to the specific embodiments of the disclosure described herein. Such equivalents are intended to be encompassed by the following claims.

What is claimed is:

1. A method for providing a diagnosis or prognosis of a subject with a head injury, comprising:
   (a) providing a biological sample from the subject,
   (b) determining the concentration of osteopontin (OPN) in the sample, and
   (c) comparing the determined OPN concentration with at least one reference value, wherein the at least one reference value is an OPN cut-off valued determined by a receiver operating curve (ROC) analysis from biological samples of a patient group, and wherein the OPN cutoff-value is at least twice the value of control samples of a group of control subjects, and
   wherein an elevated OPN value is an indication that the subject has a traumatic brain injury (TBI).

2. The method of claim 1, wherein the subject is a pediatric subject.

3. The method of claim 1, wherein the subject is an adult subject.

4. The method of claim 1, wherein the reference value is the median OPN concentration of the control samples of the group of control subjects.

5. The method of claim 1, further comprising determining in the sample the concentration of GFAP, UCH-L1, S-110, inflammatory cytokines, or a combination thereof.

6. The method of claim 1, wherein the sample is selected from the group consisting of blood, plasma, serum, urine, sputum, and perspiration.

7. The method of claim 6, wherein the sample is blood plasma or blood serum.

8. The method of claim 1, wherein determining the concentration of OPN is carried out using an immunodetection method.

9. The method of claim 1, wherein the OPN concentration of the subject with a head injury is elevated compared to the reference value, further comprising treating the subject for TBI.

10. The method of claim 1, wherein an elevated OPN value in a pediatric subject is an indication that the subject has an Abusive Head Trauma (AHT).

11. The method of claim 1, wherein the OPN value is used to predict the severity of TBI.

12. A method for providing a diagnosis or prognosis of a subject with a head injury, comprising:
    (a) providing a biological sample from the subject;
    (b) determining the concentration of osteopontin (OPN) in the sample; and
    (c) comparing the determined OPN concentration with at least one reference value, wherein the at least one reference value is an OPN cut-off valued determined by a receiver operating curve (ROC) analysis from biological samples of a patient group, and wherein the OPN cutoff-value is higher than 100 ng/ml plasma; and
    wherein an elevated OPN value is an indication that the subject has a traumatic brain injury (TBI).

13. The method of claim 12, wherein the subject is a pediatric subject.

14. The method of claim 12, wherein the subject is an adult subject.

15. The method of claim 12, wherein the reference value is the median OPN concentration of control samples of a group of control subjects.

16. The method of claim 12, further comprising determining in the sample the concentration of GFAP, UCH-L1, S-110, inflammatory cytokines, or a combination thereof.

17. The method of claim 12, wherein the sample is selected from the group consisting of blood, plasma, serum, urine, sputum, and perspiration.

18. The method of claim 17, wherein the sample is blood plasma or blood serum.

19. The method of claim 12, wherein determining the concentration of OPN is carried out using an immunodetection method.

20. The method of claim 12, wherein the OPN concentration of the subject with a head injury is elevated compared to the reference value, further comprising treating the subject for TBI.

21. The method of claim 12, wherein an elevated OPN value in a pediatric subject is an indication that the subject has an Abusive Head Trauma (AHT).

22. The method of claim 12, wherein the OPN value is used to predict the severity of TBI.

* * * * *